United States Patent
Johnson et al.

(10) Patent No.: US 11,931,220 B2
(45) Date of Patent: *Mar. 19, 2024

(54) WAX-BASED COMPOSITIONS, ARTICLES MADE THEREFROM, AND METHODS OF MANUFACTURE AND USE

(71) Applicant: ULTRADENT PRODUCTS, INC., South Jordan, UT (US)

(72) Inventors: Steven B. Johnson, Magna, UT (US); David Lawrence Margetts, Salt Lake City, UT (US); Barry Lee Hobson, Grantsville, UT (US); Jonathan D. Scoville, Sandy, UT (US); Neil T. Jessop, Sandy, UT (US); Peter M. Allred, Bluffdale, UT (US); Dan E. Fischer, Sandy, UT (US)

(73) Assignee: ULTRADENT PRODUCTS, INC., South Jordan, UT (US)

(*) Notice: Subject to any disclaimer, the term of this patent is extended or adjusted under 35 U.S.C. 154(b) by 152 days.

This patent is subject to a terminal disclaimer.

(21) Appl. No.: 16/844,220

(22) Filed: Apr. 9, 2020

(65) Prior Publication Data

US 2020/0229910 A1    Jul. 23, 2020

Related U.S. Application Data

(63) Continuation of application No. 14/772,967, filed as application No. PCT/US2014/022032 on Mar. 7, 2014, now Pat. No. 10,646,318.

(Continued)

(51) Int. Cl.
*A61C 19/06* (2006.01)
*B29B 7/00* (2006.01)
(Continued)

(52) U.S. Cl.
CPC .............. *A61C 19/066* (2013.01); *B29B 7/00* (2013.01); *B29C 45/0001* (2013.01);
(Continued)

(58) Field of Classification Search
CPC ..... A61C 19/066; A61C 19/06; A61C 19/063; B29B 7/00; B29C 45/0001;
(Continued)

(56) References Cited

U.S. PATENT DOCUMENTS 2,298,846 A   10/1942   Skooglund
2,577,816 A   12/1951   Schneider et al.
(Continued)

FOREIGN PATENT DOCUMENTS

AU   2018232963 A1   10/2018
CA      2726043 A1   12/2009
(Continued)

OTHER PUBLICATIONS

Nevada State Athletic Commission "Mouth Guard Study". May 15, 2008. Accessed via boxing.nv.gov/uploadedFiles/boxingnvgov/content/HotTopics/MouthGuardStudy.pdf on Jun. 8, 2022 (Year: 2008).*

(Continued)

*Primary Examiner* — Edward Moran
(74) *Attorney, Agent, or Firm* — Workman Nydegger

(57) ABSTRACT

Wax-based compositions for making barrier layers used in oral treatment devices are thermally stable when formed into a flat sheet or three-dimensional article to a temperature of at least 45° C. and are plastically deformable at room temperature (25° C.). The wax-based compositions include a wax fraction homogeneously blended with a polymer fraction. The wax fraction includes at least one wax and the polymer fraction includes at least one polymer selected such that, when the at least one wax and at least one polymer are (Continued)

homogeneously blended together, they yield a wax-based composition having the desired properties of thermal stability and plastic deformability. Barrier layers and oral treatment devices made from such wax-based compositions are dimensionally stable to a temperature of at least 40° C. without external support and can be plastically deformed in a user's mouth to become at least partially customized to the size and shape of user's unique dentition.

27 Claims, 7 Drawing Sheets

Related U.S. Application Data

(60) Provisional application No. 61/799,532, filed on Mar. 15, 2013, provisional application No. 61/775,453, filed on Mar. 8, 2013.

(51) Int. Cl.
  *B29C 45/00* (2006.01)
  *B29C 48/00* (2019.01)
  *C08L 91/08* (2006.01)
  *B29K 91/00* (2006.01)
  *B29L 31/00* (2006.01)

(52) U.S. Cl.
  CPC ............ *B29C 48/001* (2019.02); *C08L 91/08* (2013.01); *B29K 2091/00* (2013.01); *B29K 2995/0077* (2013.01); *B29K 2995/0081* (2013.01); *B29L 2031/753* (2013.01)

(58) Field of Classification Search
  CPC ...... B29C 47/0038; C08L 23/00; C08L 91/08; B29K 2091/00; B29K 2995/0077; B29K 2995/0081; B29L 2031/753
  See application file for complete search history.

(56) References Cited

U.S. PATENT DOCUMENTS

| | | | |
|---|---|---|---|
| 2,582,037 A | 1/1952 | Hyde | |
| 2,707,951 A | 5/1955 | Shackelford | |
| 2,773,045 A | 12/1956 | Simeri et al. | |
| 3,326,835 A | 6/1967 | Signorelli et al. | |
| 3,745,033 A | 7/1973 | Hutchison | |
| 4,614,758 A | 9/1986 | Schwabe | |
| 5,299,936 A | 4/1994 | Ueno | |
| 5,339,832 A | 8/1994 | Kittelsen | |
| 5,810,961 A | 9/1998 | Andersen | |
| 6,302,686 B1 | 10/2001 | Chott et al. | |
| 6,358,043 B1 | 3/2002 | Mottate et al. | |
| 6,629,841 B1 | 10/2003 | Skinner | |
| 7,625,210 B2 | 12/2009 | Allred et al. | |
| 7,645,137 B2 | 1/2010 | Wasyluch | |
| 7,775,214 B1 | 8/2010 | Lesniak et al. | |
| 7,959,902 B1 | 6/2011 | Postlewaite | |
| 8,113,837 B2 | 2/2012 | Zegarelli | |
| 8,277,215 B2 | 10/2012 | McLean et al. | |
| 8,357,795 B2 | 1/2013 | Lebreton | |
| 8,944,819 B2 | 2/2015 | Faasse | |
| 8,956,160 B2 | 2/2015 | Willison | |
| 9,789,036 B2 | 10/2017 | Jensen | |
| 10,646,318 B2 | 5/2020 | Johnson et al. | |
| 2003/0075184 A1 | 4/2003 | Persichetti | |
| 2003/0088011 A1 | 5/2003 | Kamohara | |
| 2003/0205234 A1* | 11/2003 | Bardach ................ | A61J 7/0053 128/861 |
| 2004/0005277 A1* | 1/2004 | Willison .............. | A61C 19/063 424/53 |
| 2004/0038171 A1 | 2/2004 | Jacobs et al. | |
| 2005/0260544 A1 | 11/2005 | Jones et al. | |
| 2006/0078848 A1 | 4/2006 | Fischer et al. | |
| 2006/0233865 A1 | 10/2006 | Odajima | |
| 2007/0298380 A1 | 12/2007 | Allred | |
| 2008/0050693 A1 | 2/2008 | Fischer et al. | |
| 2008/0081852 A1 | 4/2008 | Kamohara et al. | |
| 2009/0305184 A1 | 12/2009 | Ting | |
| 2010/0028829 A1 | 2/2010 | Lewis | |
| 2010/0112510 A1 | 5/2010 | Wasylucha | |
| 2010/0269836 A1 | 10/2010 | Roettger | |
| 2011/0171066 A1 | 7/2011 | Captain et al. | |
| 2011/0171605 A1 | 7/2011 | McLean et al. | |
| 2011/0171606 A1 | 7/2011 | Lewis et al. | |
| 2011/0189637 A1 | 8/2011 | Andersen | |
| 2011/0207087 A1 | 8/2011 | Jones | |
| 2012/0214904 A1 | 8/2012 | Prusty et al. | |
| 2012/0325224 A1* | 12/2012 | Elkin .................. | A63B 71/085 128/862 |
| 2013/0184390 A1 | 7/2013 | Bhakta | |
| 2013/0298916 A1 | 11/2013 | Alvarez | |
| 2014/0196725 A1* | 7/2014 | Maurello ................ | A61C 1/00 128/861 |
| 2014/0335467 A1 | 11/2014 | Yamamoto et al. | |
| 2015/0374464 A1 | 12/2015 | Stewart | |
| 2016/0015496 A1 | 1/2016 | Johnson | |
| 2016/0230007 A1 | 8/2016 | Johnson et al. | |
| 2022/0117865 A1* | 4/2022 | Sagel ..................... | A61Q 11/00 |

FOREIGN PATENT DOCUMENTS

| | | | |
|---|---|---|---|
| CN | 85101852 | | 1/1987 |
| CN | 1343109 | A | 4/2002 |
| CN | 1708382 | | 12/2005 |
| CN | 1791368 | A | 6/2006 |
| CN | 1913867 | A | 2/2007 |
| CN | 201147381 | Y | 11/2008 |
| CN | 101869510 | A | 10/2010 |
| CN | 101909582 | A | 12/2010 |
| CN | 201692090 | U | 1/2011 |
| GB | 0980405 | A | 1/1965 |
| JP | 60-240762 | A | 11/1985 |
| JP | 200319240 | | 1/2003 |
| JP | 2003019240 | * | 1/2003 |
| JP | 2004538085 | | 12/2004 |
| JP | 2007-503251 | A | 2/2007 |
| JP | 2009-084326 | * | 4/2009 |
| JP | 200984326 | | 4/2009 |
| JP | 2009084326 | | 4/2009 |
| JP | 2009-189447 | A | 8/2009 |
| JP | 2010-75644 | | 4/2010 |
| JP | 2010-535584 | A | 11/2010 |
| WO | 93/02860 | A1 | 2/1993 |
| WO | 2005/023142 | A1 | 3/2005 |
| WO | 2006/050108 | A1 | 5/2006 |
| WO | 2006/052593 | A2 | 5/2006 |
| WO | 2012081396 | | 6/2012 |
| WO | 20130173100 | | 11/2013 |
| WO | 2014138659 | | 9/2014 |

OTHER PUBLICATIONS

Conrad, Robin. "Styrene-Ethylene-Butylene-Styrene Thermoplastic Elastomer (SEBS)". Jun. 23, 2021. Accessed via elastomer.kuraray.com/us/blog/sebs/ on Jun. 8, 2022 (Year: 2021).*
ExxonMobil "Vistamaxx performance polymers". 2022. Accessed via https://www.exxonmobilchemical.com/en/products/polymer-modifiers/vistamaxx-performance-polymers on Jun. 8, 2022 (Year: 2022).*
Quinchia et al. "Viscosity modification of different vegetable oils with EVA copolymer for lubricant applications", Industrial Crops and Products 32 (2010) 607-612 (Year: 2010).*
Structure Probe Inc., 'Parafilm® M Barrier Film' 2010; figure 2; p. 1, paragraphs 3-4; p. 2, paragraphs 2, 7.
Mixture—definition of mixture in English_Oxford Dictionaries.
Star Thermoplastics, "Thermoplastic vs. Thermostet" retrieved from internet Jun. 22, 2017.
Engineers Handbook, "Engineering Materials—Thermoset Plastics—Silicone", retrieved from internet Jun. 22, 2017.

(56) References Cited

OTHER PUBLICATIONS

Carey, Francis A., "Organic Chemistry" Second Edition, 1992.
Wikipedia Definition of Polymer; downloaded May 24, 2018.
U.S. Appl. No. 14/772,96, filed Nov. 3, 2016, Office Action.
U.S. Appl. No. 14/772,967, filed Feb. 9, 2017, Office Action.
U.S. Appl. No. 14/772,967, filed Jun. 28, 2017, Final Office Action.
U.S. Appl. No. 14/772,967, filed Sep. 3, 2019, Office Action.
U.S. Appl. No. 15/027,636, filed Mar. 21, 2019, Office Action.
U.S. Appl. No. 14/772,967, filed Jan. 29, 2020, Notice of Allowance.
U.S. Appl. No. 15/027,636, filed Oct. 24, 2019, Office Action.
Australian Office Action cited in Australian Application No. 2014225412 dated Jan. 5, 2018.
"EPO Extended Search Report cited in EP Application No. EP105485KG900pb dated Aug. 6, 2017."
"Parafilm(Registered) M Barrier Film", Aug. 11, 2010 (Oct. 11, 2010), p. 2, XP055333981.
Anonymous "Product Information Sheet: Parafilm M—P7793, P 7543, P 7668 and P 6543" Oct. 1, 2003, 1 page.
Engineers Handbook, "Engineering Materials—Thermoset Plasitcs—Silicone", retreived from internet Jun. 22, 2017.
International Search Report and Written Opinion for PCT/US2014/022053, dated Jul. 8, 2014.
International Search Report and Written Opinion issued in PCT Application No. PCT/US2014/022032 dated Aug. 27, 2014.
Star Thermoplastics, "Thermoplastic vs. Thermostet" retrived from internet Jun. 22, 2017.
Structure Probe Inc.: Parafilm M Barrier Film; Aug. 11, 2010, p. 2, paragraph 7.

\* cited by examiner

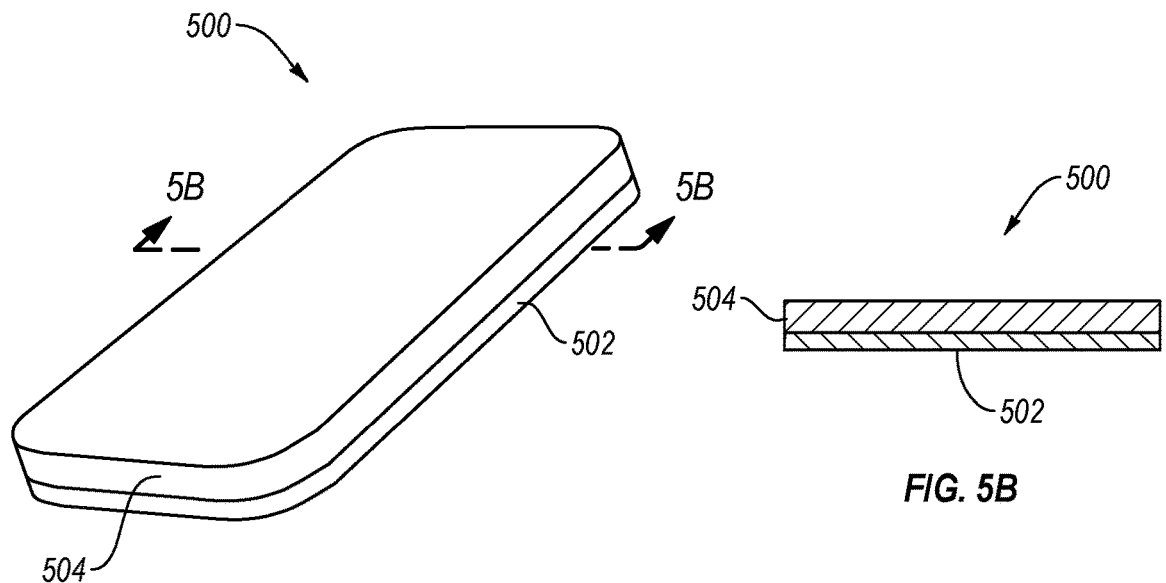
FIG. 5A
FIG. 5B
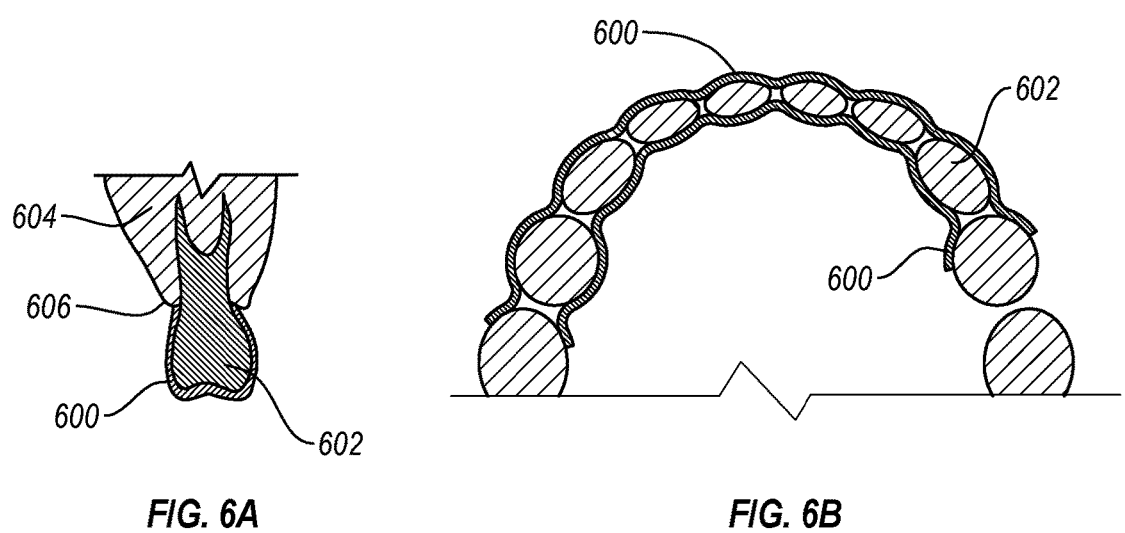
FIG. 6A
FIG. 6B

WAX-BASED COMPOSITIONS, ARTICLES MADE THEREFROM, AND METHODS OF MANUFACTURE AND USE

CROSS-REFERENCE TO RELATED APPLICATIONS

This application is a continuation of U.S. patent application Ser. No. 14/772,967, filed Sep. 4, 2015, which is a 371 Application of International Patent Application No. PCT/US14/022032, filed Mar. 7, 2014, which claims the benefit of U.S. Provisional Patent Application No. 61/799,532, filed Mar. 15, 2013, and U.S. Provisional Patent Application No. 61/775,453, filed Mar. 8, 2013, which are incorporated by reference in their entirety.

BACKGROUND OF THE INVENTION

1. The Field of the Invention

The present invention is in the field of wax-based compositions and dental treatment devices and other articles made from such compositions.

2. The Relevant Technology

Dental treatment trays and strips are commonly used to deliver bleaching compositions and medicaments to a user's teeth. "Trays" are pre-shaped barriers designed to fit over some or all of a user's teeth and can be customized or non-customized. Trays can be pre-loaded with an oral treatment composition or filled with a treatment composition by the user at the time of use. "Strips" are generally non-customized sheet-like barriers that include a treatment composition on one side or embedded within the barrier layer and which can be placed over and folded around a user's teeth in a tray-like configuration.

One type of customized dental tray is made by thermoforming a sheet of moisture-resistant thermoplastic polymer material, such as ethylene vinyl acetate copolymer (EVA), over a stone model of a user's teeth and then trimming the intermediate molded form to yield the desired tray-like shape. A block out material can be applied to the stone model to form reservoirs in the customized tray, which can accommodate placement of additional treatment composition next to a person's tooth surfaces. Reservoirs can provide additional comfort by reducing orthodontic forces, particularly with more rigid trays. Drawbacks of customized trays formed in this manner include the time and cost of forming an impression of a person's teeth, typically at a dentist office, using the impression to form the stone model, thermoforming the sheet, and trimming the molded form to yield the customized tray. The main benefit is that such trays typically provide the best fit, comfort and effectiveness in delivering a medicament to a user's teeth as compared to oral strips and other types of dental trays.

Another type of customized tray is made using a person's own teeth as the template (e.g., so called "boil-and-bite" trays). In a typical customization process a non-customized tray blank made from a thermally softenable polymer material is initially heated (e.g., in hot water or microwave oven) to temporarily soften the polymer tray material. The softened tray is then placed over the user's teeth and customformed to the user's teeth using forces applied by one or more of biting, suctioning, or externally applied pressure using fingers. When the customized tray has cooled sufficiently to retain its form, it can be removed from the user's mouth and is then ready for use. A drawback of self-customized trays is that they can be bulky and uncomfortable, particularly when in the form of sports mouth guard, which typically have a wall thickness of at least 3 mm and usually more. And while there have been patents directed to thin-walled, self-customizable trays, such trays can be difficult for a non-dental practitioner to use, have poor fit, and have had little market acceptance.

Non-customized trays lack features corresponding to a user's unique dentition but can be made to roughly approximate the size and shape of a variety of differently sized and shaped dental arches. A major drawback of non-customized trays is poor fit. Thicker walled trays can be bulky, uncomfortable and often have large gaps between the side walls and the user's tooth surfaces. Thinner, more flexible trays can better adapt to the shape of a user's teeth but have their own drawbacks. The thinnest and most comfortable of such trays can be flimsy and difficult to install and are more easily dislodged during use compared to custom-fitted trays or more rigid non-customized trays. Thin-walled trays made from materials that are sufficiently rigid and/or resilient so as to better maintain their tray-like shape and facilitate installation over a user's teeth tray are less adaptable and have tray walls that are more likely to pull away from a user's teeth during use, particularly the lingual wall. This can be both annoying to the user and permit ingress of saliva into the trough, which can cause diffusion of treatment composition into the person's oral cavity.

Conventional dental treatment strips typically comprise a flexible plastic barrier layer coated or impregnated with a treatment composition on the side of the strip facing the user's teeth. To install the strip, a portion of the strip is placed over the front surfaces of the user's teeth and the remainder is folded around the occlusal edges of the teeth and against the lingual surfaces. A drawback of strips is that they are generally more difficult to install over a user's teeth in the proper location compared to trays, which already have a trough into which the teeth are to be placed, which directs correct installation. Nevertheless, a properly placed strip can remain in place and provide a high level of comfort during treatment, perhaps even more comfort than a dental tray. An improperly placed strip, however, can fail to properly cover all tooth surfaces to be treated, may require adjustment, and can permit treatment composition to rapidly diffuse into the user's oral cavity. Moreover, strips with less adhesive treatment compositions are prone to slip off the teeth during use as a result of even minimal movement of the user's mouth, jaw or tongue. It is usually recommended that users not eat, drink, smoke or sleep while wearing the treatment strip. In some cases, the strip can become so dislodged or mangled that it must be removed and replaced with a fresh strip to complete the desired treatment.

Ultimately, the main impediment to successful treatment is the failure of a user to complete the prescribed treatment regimen. If the treatment apparatus is uncomfortable to wear, difficult to install and/or is prone to prematurely dislodge from the user's teeth, the user may simply give up and prematurely abort the prescribed regimen. Thus, even if dental treatments are possible using a particular treatment apparatus or method, they are less likely to be properly completed if the inadequacies of the treatment apparatus or method cause a user to become discouraged before the desired results are attained.

BRIEF SUMMARY

Disclosed herein are wax-based compositions suitable for making sheets or articles that are thermally stable and plastically deformable. Example wax-based compositions include a wax fraction comprised of at least one wax and a polymer fraction homogeneously blended with the wax fraction comprised of at least one polymer. According to one embodiment, the wax-based composition is plastically deformable at room temperature (25° C.) and thermally stable when formed into a flat sheet or three-dimensional article to a temperature of at least 40° C., or at least about 42.5° C., or at least about 45° C., or at least about 48° C., or at least about 50° C., or at least about 52.5° C., or at least about 55° C., or at least about 60° C., or at least about 65° C., or at least about 70°.

Also disclosed is a method of manufacturing a wax-based composition that is suitable for making sheets or articles that are thermally stable and plastically deformable, wherein the method comprises: (1) combining a least one wax and at least one polymer to form a mixture; and (2) processing the mixture to form a wax-based composition (a) that is comprised of a wax fraction homogeneously blended with a polymer fraction, (b) that is thermally stable when formed into a flat sheet or three-dimensional article to a temperature of at least 45° C., and (c) that is plastically deformable at room temperature (25° C.).

Flat sheets and three-dimensional articles made from wax-based compositions as disclosed herein can be used for any desired use, an example of which is as a barrier layer forming part on oral treatment device. According to one embodiment, the barrier layer can be in the form of a dental treatment tray having at least one side wall and at least one bottom wall extending laterally from the at least one side wall. According to another embodiment, the barrier layer can be in the form of a strip. The oral treatment devices include an oral treatment composition that includes one or more active agents for providing a desired oral treatment.

According to one embodiment, barrier layers made from wax-based compositions are non-customized and devoid of features corresponding to user's unique dentition. Because of the unique properties of wax-based compositions disclosed herein, the barrier can be at least partially customizable when placed into the user's mouth and heated to body temperature so as to at least partially conform to the user's unique dentition, particularly the occlusal surfaces. In this way, the oral treatment device can be self-customized by a user during use. This eliminates the need to first perform a customization procedure prior to placing an oral treatment composition adjacent to the barrier layer in order to obtain a device that closely conforms to a user's unique dentition so as to function as an at least partially customized oral treatment device. And to the extend the wax-based composition forming the barrier layer is not elastic but is plastically deformable, once the tray is fitted over a user's teeth there is less likelihood that the barrier layer will pull away from the user's teeth, as often occurs in the case of flexible barrier layers made from a resilient and/or elastomeric material.

These and other advantages and features of the present invention will become more fully apparent from the following description and appended claims or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings, in which:

FIGS. 5A-5B illustrate an oral treatment device that includes a barrier layer in the form of an initially flat strip coated with an oral treatment composition;

FIGS. 6A-6B illustrate an oral treatment strip wrapped around and closely conforming to the shape of a user's teeth as a result of the highly adaptive nature of the wax-based barrier layer and adhesive nature of the oral treatment composition.

DETAILED DESCRIPTION OF THE PREFERRED EMBODIMENTS

I. Introduction

Figure 1A:
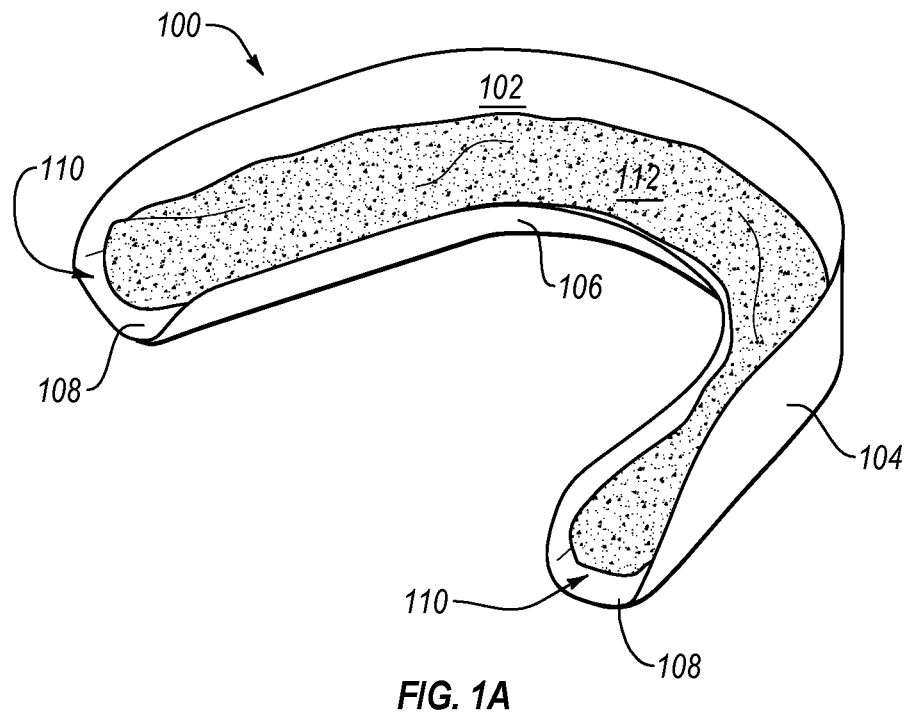
FIGS. 1A-1B illustrate exemplary oral treatment devices that include a dental treatment tray and a gel or solid oral treatment composition within the tray.

Disclosed herein are wax-based compositions formed from a wax component and a polymer component so as to be both thermally stable and plastically deformable. Because the wax-based compositions are thermally stable, articles made therefrom are able to maintain their shape without significant deformation (i.e., are dimensionally stable) in the absence of external forces when heated to temperatures at which such articles may be exposed. Because the wax-based compositions are plastically deformable, articles made therefrom are able to be plastically deformed by application of a deformation force.

Also disclosed are methods of manufacturing wax-based compositions from one more types of wax, one or more types of polymers, and optionally one or more auxiliary components so as to have desired materials and/or mechanical properties. The one or more types of wax and one or more types of polymers can be homogeneously blended together to form wax-based compositions containing a wax fraction and a polymer fraction. Heat and/or pressure can be applied to yield a wax-based composition having the desired materials and/or mechanical properties.

Example articles that can be made from wax-based compositions as disclosed herein include sheets and three-dimensional forms. The sheets and three-dimensional articles can be thermally stable and plastically deformable. The sheets can be used for any desired purpose, examples of which include as a barrier layer in an oral treatment strip used to apply an oral treatment composition to a user's teeth and/or gums, as an intermediate substrate that is thermoformed into a dental treatment tray, and as a covering for reversibly sealing an orifice of a container. Examples of useful three-dimensional articles include dental treatment trays, such as those made by injection molding the wax-based composition or thermoforming a wax-based sheet.

Oral treatment devices are an example of a specific application of example articles made from wax-based compositions as disclosed herein. Oral treatment devices can include a barrier layer, such as a strip or tray, and one or more oral treatment compositions adjacent to and/or impregnated within the barrier layer. An example oral treatment strip includes a wax-based sheet that is initially flat and includes an oral treatment composition adjacent to and/or impregnated within the sheet. The oral treatment strip can be placed over and wrapped around at least a portion of a user's teeth. Another example of an oral treatment device includes a preformed dental treatment tray formed from a wax-based composition and an oral treatment composition placed and/or impregnated within the dental treatment tray. The preformed dental treatment tray facilitates greater ease of placement of the oral treatment device over a person's teeth compared to an oral treatment strip.

According to one embodiment, an oral treatment device includes a barrier layer that is initially non-customized and devoid of features corresponding to a user's unique dentition but which can adapt to the person's teeth during use. According to one embodiment, the barrier layer is at least partially customizable when warmed to body temperature and shaping forces are applied, such as suctioning, biting and/or finger pressure. In this way, a self-customizable oral treatment device is provided that can be self-customized in a user's mouth after placement of an oral treatment composition on or in the barrier layer. This greatly facilitates oral treatment because it provides a comfortable fitting, customized device that can be made during oral treatment. This eliminates cumbersome customization procedures and time delays typically involved in making customized trays, whether using a stone model of a person's teeth or in a "boil and bite" procedure. Customization has heretofore required customization prior to applying the oral treatment composition on or in a customized dental tray. The ability of oral treatment devices that already include a treatment composition to be self-customized in the user's mouth is surprising and unexpected, which further emphasizes the unique and inventive nature of wax-based compositions as disclosed herein.

Kits are also provided that utilize barrier layers made from wax-based compositions as disclosed herein and oral treatment devices that include barrier layers and one or more oral treatment compositions adjacent to or impregnated within the barrier layer. Kits may include multiple oral treatment devices that include a barrier layer and one or more pre-applied oral treatment compositions. Alternatively, kits may include one or more oral treatment devices that include a barrier layer and one or more oral treatment compositions that can be applied to the barrier layer by a user.

Methods of providing treatment to a user's teeth and/or gums utilize barrier layers made from wax-based compositions as disclosed herein and one or more oral treatment compositions that are pre-applied to the barrier layer or which can be applied to the barrier layer by a user at the time of use. According to one embodiment, a user places an oral treatment device that includes a wax-based barrier layer and an oral treatment composition into the user's mouth and then plastically deforms the wax-based barrier layer to better conform to the user's unique dentition in order to provide better fit and comfort. The oral treatment device can be self-customizable by the user as described herein, such as by warming the wax-based barrier layer to body temperature within the user's mouth and applying forces to plastically deform the barrier layer in order to at least partially customize the barrier layer so as to include indentations that conform to the user's unique dentition.

II. Wax-Based Compositions

Wax-based compositions as disclosed herein include a wax fraction, a polymer fraction homogeneously blended with the wax fraction, and optionally one or more auxiliary components. Examples of waxes that can be used include petroleum waxes, distilled waxes, synthetic waxes, mineral waxes, vegetable waxes, and animal waxes. Examples of polymers that can be used include synthetic and natural polymers. Examples of auxiliary components include plasticizers, flow modifiers, and fillers.

Examples of petroleum waxes include paraffin waxes (made of long-chain alkane hydrocarbons) (e.g., IGI 1260A), intermediate waxes (blend of long-chain and branched alkanes), microcrystalline waxes (branched alkane hydrocarbons of higher molecular weight and more amorphous than paraffin waxes) (e.g., IGI 5909A), distilled waxes (e.g., Astorstat® distilled waxes, such as Astorstat 6988, Astorstat 6920, 10069, Astorstat Astorstat 95, Astorstat 90, Astorstat 75, and Astorstat 10316), and petroleum jelly.

Examples of synthetic waxes include polyethylene waxes (based on polyethylene), Fischer-Tropsch waxes (made from synthesis gas), chemically modified waxes (which are usually esterified or saponified), substituted amide waxes, and polymerized α-olefins. Examples of mineral waxes include ceresin waxes, montan wax (extracted from lignite and brown coal), ozocerite (found in lignite beds), and peat waxes.

Examples of vegetable waxes include bayberry wax (from the surface wax of the fruits of the bayberry shrub, *Myrica faya*), candelilla wax (from the Mexican shrubs *Euphorbia cerifera* and *Euphorbia antisyphilitica*), carnauba wax (from the leaves of the Carnauba palm, *Copernica cerifera*), castor wax (catalytically hydrogenated castor oil), esparto wax (a byproduct of making paper from esparto grass, *Macrochloa tenacissima*), Japan wax (a vegetable triglyceride, from the berries of *Rhus* and *Toxicodendron* species), jojoba oil (pressed from the seeds of the jojoba bush, *Simmondsia chinensis*), ouricury wax (from the Brazilian feather palm, *Syagrus coronata*), rice bran wax (obtained from rice bran, *Oryza sativa*), and soy wax (from soybean oil). Examples of animal waxes include beeswax (produced by honey bees), Chinese wax (produced by the scale insect *Ceroplastes ceriferus*), lanolin (wool wax, from the sebaceous glands of sheep), and shellac wax (from the lac insect *Kerria lacca*).

Blends of waxes can be useful to incorporate materials properties from the different waxes. For example, paraffin wax, intermediate wax, and/or microcrystalline wax can be blended to provide a desired level of plastic deformation at room temperature and dimensional stability at higher temperatures. Paraffin, intermediate and microcrystalline waxes are all fully saturated hydrocarbon mixtures with the formula $C_nH_{2n+2}$. Paraffin waxes predominately include straight-chain alkanes, microcrystalline waxes predominately include branched alkanes of higher molecular weight than the alkanes in paraffin wax, and intermediate waxes have components and properties intermediate to those of paraffin and microcrystalline waxes. The effect of branching is to reduce melting point and increase viscosity. In general, paraffin waxes comprise mostly linear C18 to C40 alkanes, intermediate waxes have increased branching and comprise mostly C25 to C60 alkanes, and microcrystalline waxes contain little or no linear alkanes but rather complex, branched C25 to C85 alkanes.

As a general rule, the properties of paraffin wax and microcrystalline waxes can be generalized as follows:

| Paraffin Wax | Microcrystalline Wax |
|---|---|
| Low melting | Higher melting |
| White | Colored |
| Hard | Soft |
| Brittle | Malleable |
| Translucent | Opaque |
| Crystalline | Amorphous |
| Glossy | Adhesive |

The one or more waxes comprising the wax fraction of wax-based compositions as disclosed herein are typically included in an amount in a range of about 40% to about 95% by weight, preferably in a range of about 50% to about 93% by weight, more preferably in a range of about 60% to about 90% by weight, and most preferably in a range of about 70% to about 85% by weight of the wax-based composition.

The polymer fraction can include at least one type of polymer, examples of which include one or more polymers selected from polyolefins, polyesters, polyurethanes, thermoplastic elastomers, thermoset elastomers, and mixtures thereof. Examples of polyolefins include polyethylene (including high density polyethylene, HDPE), low density polyethylene, LDPE, or ultralow density polyethylene, ULDPE), polypropylene (PP), and polytetrafluoroethylene (PTFE) (e.g., TEFLON), thermoplastic polyolefins (e.g., thermoplastic polyethylene, thermoplastic polypropylene, thermoplastic olefins), and propylene-based elastomers. Other synthetic polymers include ethylene-vinyl acetate copolymer (EVA), ethylene-vinyl alcohol copolymer (EVAL), polyvinyl acetate, polyvinyl alcohol, polyesters (such as polyethylene terephthalate, or PETE), polycarbonates, methacrylates, acrylates, polyamides (e.g., nylon), polyurethanes, polyvinyl chloride (PVC), synthetic rubber, phenol formaldehyde resin (Bakelite), neoprene, polystyrene, polyacrylonitrile, PVB, silicone elastomers, and thermoplastic elastomers (e.g., olefin-based elastomers, such as ethylene-, propylene- or butylene-based elastomers) (e.g., Engage™ thermoplastic elastomers, Vistamaxx™ thermoplastic elastomers, such as Vistamaxx™ 6102, Vistamaxx™ 6202, and Vistamaxx™ 3020, Duragrip® DGR 6250CL, and Thermolast® M TM6LFT). Natural polymeric materials include shellac, natural rubber, polysaccharides, cellulosic ethers, cellulose acetate, and proteins.

According to one embodiment, the polymer fraction can have high peroxide stability (i.e., so as to not cause decomposition of a peroxide bleaching agent) and/or good thermal stability (i.e., so as to yield a strip or tray that maintains its shape when exposed to elevated temperatures during shipping and storage).

The one or more polymers comprising the polymer fraction of wax-based compositions as disclosed herein are typically included in an amount in a range of about 5% to about 60% by weight, preferably in a range of about 7% to about 50% by weight, more preferably in a range of about 10% to about 40% by weight, and most preferably in a range of about 15% to about 30% by weight of the wax-based composition.

When included, the one or more auxiliary components (e.g., plasticizers, flow modifiers, and/or fillers) can be included in an amount in a range of about 0.01% to about 5% by weight of the wax-based composition, preferably in a range of about 0.1% to about 4% by weight, and more preferably in a range of about 1% to about 3% by weight of the wax-based composition.

At least a portion of the wax fraction, polymer fraction and/or auxiliary component can be similar to and/or provided by the materials contained in Parafilm®, which is sold in sheet form and which contains a proprietary blend of wax and polyolefin. Parafilm® M is a flexible sheet material with a paper backing to prevent self-adhesion and is commonly used to temporarily seal flasks or cuvettes in chemistry labs. Parafilm® F is commonly used in plant grafting. Parafilm® sheets typically soften at about 100° F. (or about 38° C.) and, if a Parafilm® sheet is thermoformed into a dental treatment tray, it begins to sag at temperatures of about 38° C. and above. As a result, oral treatment strips made using native Parafilm® as a barrier layer can become crinkled or shriveled at elevated temperatures during shipping and storage (i.e., which can reach 50° C. or more). Moreover, oral treatment strips made using native Parafilm® as the barrier layer can become excessively soft and gummy when placed in the mouth and exposed to body temperature over lengthy periods of time, permitting users to easily bite through and perforate the Parafilm® barrier layer, compromising its ability to function as a barrier to saliva.

Unexpectedly, however, when Parafilm® sheet material is cut into pieces and used as a feed material in an injection molding process, the resulting injection molded trays are thermally stable to a temperature above 40° C. (e.g., up to about 50-52° C. depending on the injection molding conditions). Therefore, the composition of "native" Parafilm® is apparently transformed into a new composition of matter when subject to temperatures and/or pressures associated with injection molding processes, such as those described herein. In addition, Parafilm® can be used as a blending component together with other components disclosed herein to yield trays or strips having thermal stability at temperatures of at least 40° C.

According to several embodiments, wax-based compositions are thermally stable (i.e., are dimensionally stable and resist significant deformation) when formed into a flat sheet or a three-dimensional article and heated to a temperature to which the sheet or article is typically subjected to during transport and storage. According to one embodiment, the wax-based composition is thermally stable when heated to a temperature of at least 40° C., or at least about 42.5° C., or at least about 45° C., or at least about 48° C., or at least about 50° C., or at least about 52.5° C., or at least about 55° C., or at least about 60° C., or at least about 65° C., or at least about 70°.

In addition, the wax-based composition can be plastically deformable. That is, the composition can be formed into a desired shape and then retain that shape absent application of an external force. According to one embodiment, the wax-based composition is plastically deformable and non-brittle at room temperature (25° C.). In other words, the wax-based composition can be configured into a desired shape without breaking or cracking and so as to retain that shape without heating to above room temperature. In other embodiments, the wax-based composition becomes plastically deformable at room temperature when extruded into a sheet or thermoformed or injection molded at elevated temperature into a desired three-dimensional article of a specified thickness. In some embodiments, the wax-based composition is semi-rigid at room temperature and becomes more flexible and deformable when heated to above room temperature, such as body temperature in the case of an oral treatment device that includes a wax-based barrier layer.

Depending on the relative concentrations of the wax and polymer fractions, the wax fraction may comprise a continuous phase and the polymer fraction may comprise a disperse phase within the continuous wax phase. Alternatively, the polymer fraction may comprise a continuous phase and the wax fraction may comprise a disperse phase within the continuous wax phase. In some cases, it is possible for the wax and polymer fractions to form an interpenetrating network without continuous and disperse phases.

An exemplary method of manufacturing a wax-based composition that is suitable for making sheets or articles that are thermally stable and plastically deformable includes: (1) combining a least one wax and at least one polymer to form a mixture; and (2) processing the mixture to form a wax-based composition that is comprised of a wax fraction homogeneously blended with a polymer fraction.

According to one embodiment, the at least one type of wax and the least one type of polymer are combined and processed using an extruder (e.g., a single screw or twin screw extruder). The extruder can form the wax-based composition into the form of a sheet having a desired thickness. The sheet can be used as is or further shaped, such as by thermoforming, into a desired shape of an article of manufacture (e.g., a dental treatment tray). Alternatively, the extruder can form the wax-based composition into a strand that is cut into individual pellets, which can then be further processed, such as by injection molding, to form a desired shape of an article of manufacture. Other mixing apparatus known in the art can be used to form wax-polymer blends, which are then extruded, injection molded, or otherwise formed into a desired shape.

Example extruders can include a plurality of zones (e.g., 10 zones), such as mixing, heating and pressuring zones. The wax, polymer and auxiliary materials can be fed separately into the extruder in different zones or together in the same zone. For example, the one or more polymer components can be fed into zone 1, and the one or more wax components can be fed into zone 3. Auxiliary components, if used, can be fed into one of these zones or a different zone. The zones can have similar or different temperatures. In general, the materials fed into and mixed within the extruder can be subjected to one or more temperatures in a range of about 50° C. to about 225° C., preferably in a range of about 55° C. to about 210° C. More preferably the materials in the earlier zones are subjected to a higher temperature in a range of about 135° C. to about 220° C. and in the later zones to a lower temperature in a range of about 50° C. to about 125° C. in another part of the extruder, most preferably to a higher temperature in the earlier zones in a range of about 140° C. to about 210° C. and to a lower temperature in the later zones in a range of about 55° C. to about 120° C. The pressure within the extruder can be up to about 1000 psi, preferably up to about 100 psi, more preferably up to about 50 psi, and most preferably in a range of about 1 to about 25 psi.

Example injection molding apparatus include a hopper, a barrel with feeder screw, an injection nozzle, a valve gate, a mold cavity, and a mold core. In an injection molding process, the wax-based composition can be subjected to one or more initial temperatures for melting or softening the composition in a range of about 40° C. to about 200° C., preferably in a range of about 45° C. to about 150° C., and more preferably in a range of about 50° C. to about 120° C.

The feeder barrel can have multiple heating zones of increasing temperature. In general, the highest temperature is reached at the valve gate. The softened or melted composition is introduced into the mold cavity under pressure in order to fill the mold cavity, such as at a pressure in a range of about 1000 psi to about 50,000 psi, preferably in a range of about 2500 psi to about 40,000 psi, more preferably in a range of about 5000 psi to about 30,000 psi, even more preferably in a range of about 7500 psi to about 20,000 psi, and most preferably in a range of about 10,000 psi to about 15,000 psi. To yield a solidified injection molded article, the mold core and cavity can have a reduced temperature in a range of about −10° C. to about 40° C., preferably in a range of about −5° C. to about 30° C., more preferably in a range of about 0° C. to about 25° C., even more preferably in a range of about 2° C. to about 20° C., and most preferably in a range of about 3° C. to about 10° C.

III. Articles Made from Wax-Based Compositions

Examples of articles that can be made from wax-based compositions as disclosed herein include, but are not limited to, sheets, oral treatment strips, sheets for sealing orifices, molded three-dimensional articles, and dental treatment trays. Sheet-like articles can be flat and are flexible and plastically deformable so as to be capable of being placed over an object and then wrapped around the object into a desired configuration that is able to maintain its shape. In some cases, the sheets can "customizable" in order to include 3-dimensional features of the object around which it is wrapped. Similarly, molded three-dimensional articles can be plastically deformable so as to be capable of being placed over an object and then further adapted to better fit over the object and better conform to the three-dimensional features of the object around over which it is adapted.

According to several embodiments, flat or curved sheets are provided that are plastically deformable at room temperature (25° C.) and thermally stable at temperatures of at least 40° C., or at least about 42.5° C., or at least about 45° C., or at least about 48° C., or at least about 50° C., or at least about 52.5° C., or at least about 55° C., or at least about 60° C., or at least about 65° C., or at least about 70° (e.g., at temperatures between 50-75° C. depending on the formulation). This permits sheet-like articles made form the wax-based compositions disclosed herein to be manufactured, transported and stored at temperatures of 50-75° C. or more without losing their desired shape. The sheets comprise a wax-based composition that includes a wax fraction and a polymer fraction homogeneously blended with the wax fraction. The wax fraction includes at least one wax. The polymer fraction includes at least one polymer. The sheet can be formed by extruding the wax-based composition.

According to other embodiments, three-dimensional articles are provided that are plastically deformable at room temperature (25° C.) and thermally stable to temperatures of at least 40° C., or at least about 42.5° C., or at least about 45° C., or at least about 48° C., or at least about 50° C., or at least about 52.5° C., or at least about 55° C., or at least about 60° C., or at least about 65° C., or at least about 70° (e.g., at temperatures between 50-75° C. depending on the formulation) and are therefore dimensionally stable at elevated temperatures.

IV. Oral Treatment Devices and Kits

Disclosed herein are oral treatment devices that include a barrier layer comprised of a wax-based composition and an oral treatment composition disposed adjacent to and/or impregnated within the barrier layer. The barrier layer can be in the form of a tray or strip. A dental treatment tray typically includes at least one sidewall (e.g., at least a labial wall and optionally also a lingual wall) and a bottom wall adjacent to and extending laterally from the at least one sidewall (e.g., extending lingually from the labial wall or forming a transition or bridge between labial and lingual walls). Strip-like barriers and/or the at least one sidewall and bottom wall of a dental treatment tray comprise a wax-based composition that includes at least one wax and at least one polymer homogeneously blended with the wax. Oral treatment devices can be formed by thermoforming a wax-based sheet, injection molding a wax-based composition, or any other appropriate method known in the art.

According to several embodiments, oral treatment devices made from the wax-based compositions disclosed herein are plastically deformable at room temperature (25° C.) and thermally stable at temperatures of at least 40° C., or at least about 42.5° C., or at least about 45° C., or at least about 47.5° C., or at least about 50° C., or at least about 53° C., or at least about 55° C., or at least about 60° C., or at least about 65° C., or, or at least about 70° C. (e.g., at temperatures between 50-75° C. depending on the formulation) and are therefore dimensionally stable at elevated temperatures. This permits oral treatment devices made form the wax-based compositions disclosed herein to be manufactured, transported and stored at temperatures of 50-75° C. or more without losing their desired shape. Nevertheless, when placed into a user's mouth, dental treatment trays and strip-like barrier layers made from wax-based compositions disclosed herein can readily conform the size and shape of a user's unique dentition (e.g., are self-customizable in a user's mouth). They can readily conform to occlusal surfaces yet resisting perforation because they are not unduly softened at body temperatures.

According to one embodiment, the tray or strip can be non-customized and devoid of features corresponding to user's unique dentition. Once placed in a user's mouth, the tray or strip can warm to body temperature, which facilitates the ability of the tray or strip to at least partially conform to the user's unique dentition and thereby become at least partially customized. For example, the tray or strip can be at least partially customized in the user's mouth using shaping forces such as suctioning, biting and/or finger pressure. According to another embodiment, the tray can be customized (e.g., using a stone model of a user's teeth to register indentations in the tray corresponding to the user's unique dentition). Oral strips and trays are advantageously formulated so that it is difficult or impossible for a user to bite through the occlusal surface of the tray or strip in order to maintain a barrier to saliva.

Kits for providing oral treatments may include multiple oral treatment devices that include a wax-based barrier layer and one or more pre-applied oral treatment compositions. Alternatively, kits may include one or more wax-based barrier layers and one or more oral treatment compositions that can be applied to the barrier layers by the user at the time of use. Kits may include some barrier layers configured to fit over a person's upper teeth and other barrier layers configured to fit over a person's lower teeth.

Alternatively, a plurality of single-use, disposable customized dental treatment trays made from wax-based compositions as disclosed herein can be provided to a user in a kit. According to one embodiment, the kit of customized dental treatment trays permits the user to have the benefit of a new customized dental tray for every treatment event.

Moreover, because of the plastically deformable nature of the wax-based composition, trays made therefore can be more comfortable and better fitting than professional custom-fitted trays.

A method of manufacturing a kit of single-use, disposable customized dental treatment trays includes: (1) taking an impression of a user's teeth using an impression material; (2) making a stone model of the user's teeth from the impression of the user's teeth; (3) providing a plurality of sheets comprised of a wax-based composition as disclosed herein; (4) thermoforming the sheets using the stone model to form the plurality of customized dental treatment trays; and (5) optionally trimming away excess tray material to maximize appropriate size and fit. The single-use, disposable customized wax-based dental treatment trays can be used in a kit that includes an oral treatment composition that is loaded into the trays by the user or they can be pre-loaded with an oral treatment composition.

Regardless of its form, the barrier layer is typically moisture-resistant in order to protect the oral treatment composition from saliva in a user's mouth. Because waxes and polymers tend to be hydrophobic, wax-based compositions as disclosed herein will typically be moisture-resistant. The wax-based barrier layers will typically have a thickness in a range of about 0.025 mm to about 1.5 mm, or from about 0.05 mm to about 1.25 mm, or from about 0.075 mm to about 1 mm, or from about 0.09 mm to about 0.75 mm, or from about 0.1 mm to about 0.5 mm, or from about 0.15 mm to about 0.35 mm.

According to one embodiment, the occlusal walls of example dental treatment trays can have a greater cross-sectional thickness than the one or more sidewalls (e.g., between about 20-100% thicker, or about 30-75% thicker, or about 40-60% thicker). This provides several benefits, including the ability of the dental treatment trays to be self-customized to a user's teeth without the user biting through and perforating the occlusal wall. It can also increase dimensional stability of the dental treatment trays by providing a more rigid base to which the one or more sidewalls are attached without compromising comfort and fit. The occlusal wall is typically the last wall to contact a user's teeth during installation such that increased rigidity of the occlusal wall does not significantly decrease the ability of the thinner sidewall(s) to be customized or adapted to the user's labial and/or lingual tooth surfaces. Moreover, because the occlusal wall can be easily self-customized to the user's occlusal tooth surfaces by biting, the user can readily self-customize the occlusal wall regardless of increased thickness. And in fact, increased thickness is most beneficial in the occlusal region, which is subjected to the greatest customization forces (i.e., biting).

Another benefit of providing a thickened occlusal wall is that it facilitates injection molding of relatively thin-walled dental treatment trays from the wax-based compositions disclosed herein. Because the occlusal wall of a molded tray is typically approximately midway between the labial and lingual walls, the mold cavity in the region corresponding to a thickened occlusal wall will be wider than adjacent regions corresponding to the thinner labial and lingual walls. A wider mold cavity in the middle region of the mold facilitates injection molding by providing better flow of the softened wax-based composition throughout the mold cavity.

Oral treatment compositions can include at least one active agent, at least one tissue adhesion (or thickening) agent, a liquid or gel solvent, carrier or vehicle into which the active agent and tissue adhesion agent are dispersed, and other components and adjuvants as desired. The treatment composition may comprise continuous or discontinuous beads or layers positioned so as to contact at least a portion of a person's tooth surfaces and/or gums. Treatment compositions can have a consistency of a liquid, gel, sticky viscous gel, putty, or solid. Solids and putties can become more sticky and adhesive to teeth and/or gums when moistened with water or saliva. In some cases, the main difference between a "gel" and a "putty" or "solid" is the level of solvent or carrier within the composition. In general, the greater the concentration of solvent or carrier relative to the tissue adhesive agent, the less viscous is the composition. The lower the concentration of solvent or carrier relative to the tissue adhesion agent, the more viscous, putty-like or solid is the composition.

Examples of active agents for oral treatment compositions include dental bleaching agents, desensitizing agents, remineralizing agents, antimicrobial agents, anti-plaque agents, anti-tartar agents, gingival soothing agents, anesthetics, antioxidants, and mouth freshening agents. Examples of dental bleaching agents include aqueous hydrogen peroxide, carbamide peroxide, metal perborates (e.g., sodium perborate), metal percarbonates (e.g., sodium percarbonate), metal peroxides (e.g., calcium peroxide), metal chlorites and hypochlorites, peroxy acids (e.g., peroxyacetic acid), and peroxy acid salts.

Bleaching agents within dental bleaching compositions according to the invention can have any desired concentration, e.g., between 1-90% by weight of the dental bleaching composition. The concentration of the dental bleaching agent can be adjusted depending on the intended treatment time for each bleaching session. The bleaching agent is preferably included in an amount in a range of about 1% to about 60% by weight, more preferably in a range of about 3% to about 40% by weight, and most preferably in a range of about 5% to about 30% by weight. When a dental bleaching agent is used, the materials used to make the wax-based composition can be selected so as to not prematurely react with and destabilize the bleaching agent.

Examples of desensitizing agents include potassium nitrate, other potassium salts, citric acid, citrates, and sodium fluoride. Examples of remineralizing agents in sodium fluoride, stannous fluoride, sodium monofluorophosphate, and other fluoride salts. Examples of antimicrobial agents and preservatives include chlorhexidine, triclosan, sodium benzoate, parabens, tetracycline, phenols, cetyl pyridinium chloride, and benzalkonium chloride. An example of an anti-plaque or anti-tartar agent is pyrophosphate salts. Examples of gingival soothing agents include aloe vera, mild potassium nitrate, and isotonic solution-forming salts. Examples of anesthetics include benzocaine and lidocaine. Examples of antioxidants include vitamin A, vitamin C, vitamin E, other vitamins, and carotene. Examples of mouth freshening agents include camphor, oil of wintergreen, peppermint, spearmint, and methyl salicylate.

Tissue adhesion agents, tackifying agents, or thickening agents can include a wide variety of hydrophilic polymers. Examples include polyvinyl pyrrolidone (PVP), PVP-vinyl acetate copolymers, carboxypolymethylene (e.g., CARBOPOL, sold by Novean, Inc.), polyethylene oxide (e.g., POLYOX, made by Union Carbide), polyacrylic acid polymers or copolymers (e.g., PEMULEN, sold by Novean, Inc.), polyacrylates, polyacrylamides, copolymers of polyacrylic acid and polyacrylamide, carboxymethylcellulose, carboxypropylcellulose, cellulosic ethers, polysaccharide gums, proteins, and the like. Examples of PVPs include Kollidon 30, a polyvinyl pyrrolidone polymer sold by BASF having a molecular weight of 50,000, Kollidon VA 60, a polyvinyl pyrrolidone polymer having a molecular weight of 60,000, and Kollidon 90 F, a polyvinyl pyrrolidone polymer having a molecular weight of 1.3 million.

In the case where the oral treatment composition is a gel, the one or more tissue adhesion agents are preferably included in an amount in a range of about 1% to about 50% by weight of the treatment gel, more preferably in a range of about 3% to about 30% by weight, and most preferably in a range of about 5% to about 20% by weight.

In the case where the oral treatment composition is a putty or solid, the one or more tissue adhesion agents are preferably included in an amount in a range of about 10% to about 90% by weight of the substantially solid treatment composition, more preferably in a range of about 20% to about 80% by weight, and most preferably in a range of about 40% to about 75% by weight.

Liquids and gels, including sticky viscous gels, may include one or more liquid or gel, solvents, carriers or vehicles into which the active agent, tissue adhesion agent, and other components are dissolved or dispersed. Examples of liquid or gel solvents, carriers or vehicles include water, alcohols (e.g., ethyl alcohol), and polyols (e.g., glycerin, sorbitol, mannitol, other sugar alcohols, propylene glycol, 1,3-propandiol, polyethylene glycol, polyethylene oxide, and polypropylene glycol).

For solids or stiff putties, the concentration of solvent, carrier or vehicle will typically be attenuated compared to treatment gels. Where it is desired to convert a gel into a putty or solid composition, it may be advantageous to include one or more volatile solvents that can be removed by evaporation (e.g., water, alcohols, acetone, and other organic solvents). Because of the affinity of hydrophilic polymers for water, even treatment compositions that appear to be solid may include a significant amount of bound water (e.g., up to about 10% or more by weight of the treatment composition). In the case where the treatment composition has the consistency of a highly viscous or stiff putty, the composition will generally include a solvent, carrier or vehicle that acts as a plasticizer or softening agent.

Oral treatment compositions may optionally include other components as desired to yield treatment compositions having desired properties. Examples include bleaching agent stabilizers (e.g., EDTA, salts of EDTA, citric acid and its salts, phosphoric acid and its salts, phenolphosphonic acid and its salts, gluconic acid and its salts, alkali metal pyrophosphates, alkali metal polyphosphates, and alkyl sulfates), neutralizing agents (e.g., sodium hydroxide and triethanolamine), inorganic thickening agents (e.g., fumed silica), colorants, flavorants, sweeteners, and the like.

According to one embodiment, oral treatment devices can have a horseshoe-shaped longitudinal profile and a trough with a U-shaped cross section, as in conventional bleaching trays. Alternatively, oral treatment devices can have barrier layers with other shapes, such as flat strips that are rectangular or contoured to fold around and fit over a user's teeth.

Figure 1B:
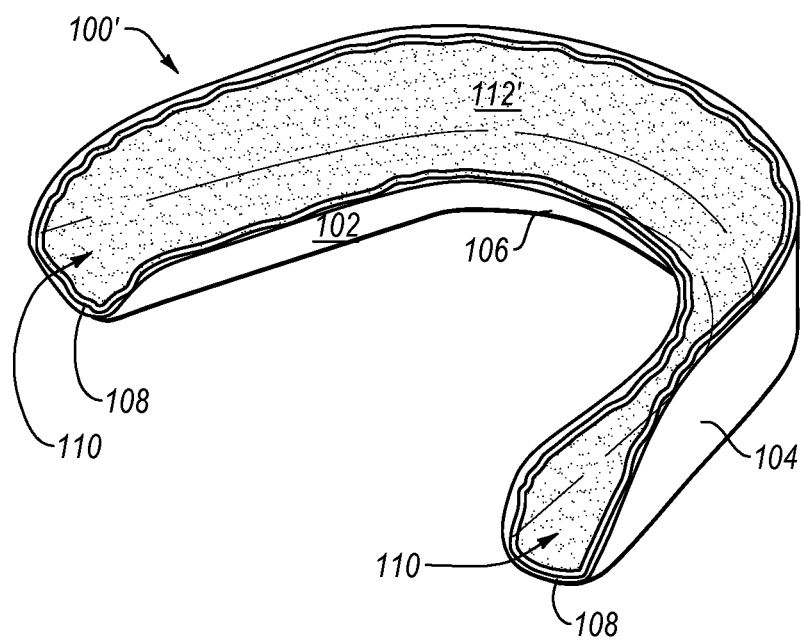

Exemplary dental treatment devices 100, 100' in the form of a tray are illustrated in FIGS. 1A and 1B. FIG. 1A is a perspective view of an oral treatment device 100 comprising a wax-based barrier layer 102 having a front side wall 104, a rear side wall 106, and a horseshoe shaped bottom wall 108 that together define a trough 110 having a generally U-shaped cross section throughout the horseshoe. Disposed within trough 110 is an oral treatment composition 112 that can be a gel, such as a sticky, viscous gel, which can assist in reliably holding the dental treatment tray in proper position over a user's teeth during use. Oral treatment composition 112 may have a consistency ranging from a gel, a sticky viscous gel, to a solid treatment composition. Oral treatment composition 112 can be a viscous gel having a cross-sectional diameter or thickness in a range of about 1 mm to about 5 mm, more preferably in a range of about 2 mm to about 4 mm. The gel can be a continuous bead of composition.

FIG. 1B depicts an oral treatment device 100' that includes a wax-based barrier layer 102 in the form of a dental tray having a horseshoe shape with a substantially U-shaped cross section. Barrier layer 102 includes front sidewall 104, rear sidewall 106, and bottom wall 108 that together define a trough 110 having a general U-shaped cross section. Within trough 110 is an oral treatment composition 112' that substantially covers the interior walls rather than being a bead of composition. Oral treatment composition 112' may be a gel, a sticky viscous gel, a putty, or a solid composition. Treatment composition 112' is preferably a stiff putty or solid having a thickness in a range of about 0.2 mm to about 2 mm, more preferably in a range of about 0.5 mm to about 1 mm.

Figure 2A:
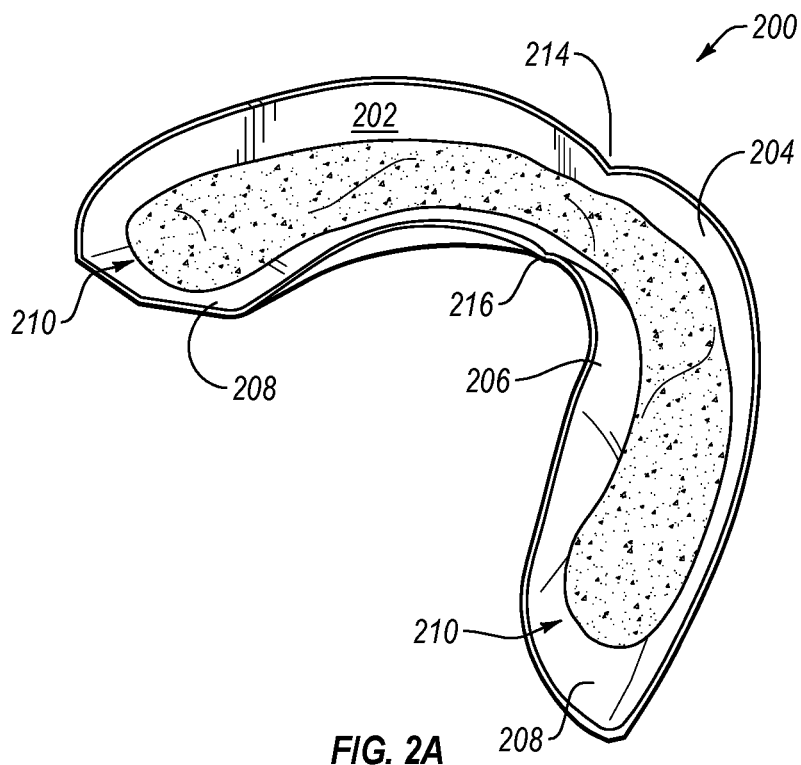
FIGS. 2A-2B illustrate exemplary oral treatment devices that include a dental treatment tray having features that assist the treatment device in conforming to the shape of a user's dental arch and a gel or solid oral treatment composition within the tray.
Figure 2B:
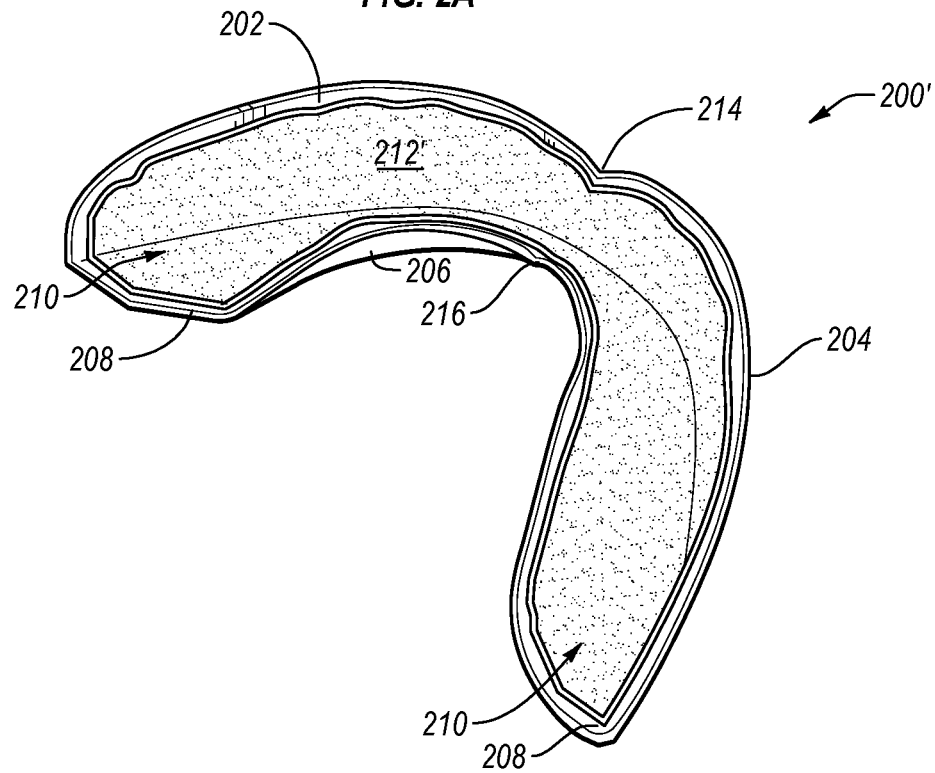

FIGS. 2A and 2B depict oral treatment devices 200, 200', each of which include a barrier layer 202 having a front sidewall 204, a rear sidewall 206, and a bottom wall 208 that together define a trough 210 into which either a bead of treatment composition 212 (FIG. 2A) or a continuous layer of treatment composition 212' (FIG. 2B) is disposed. In addition, oral treatment devices 200, 200' include a first notch 214 in front sidewall 204 and a second notch 216 in rear sidewall 206. Notches 214 and 216 assist the oral treatment devices 200, 200' in conforming to variously sized and shaped dental arches.

Figure 3A:
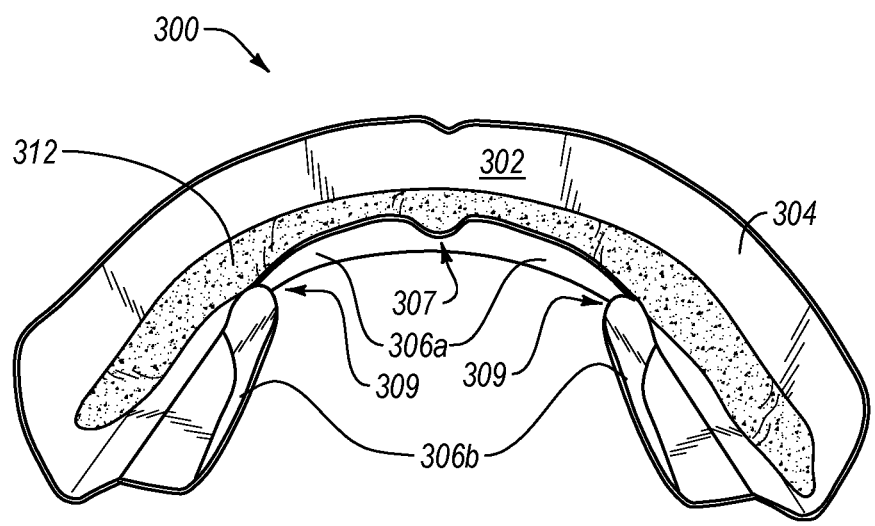
FIGS. 3A-3B illustrate exemplary oral treatment devices that include a dental treatment tray with cuts or discontinuities that assist the treatment device in conforming to the shape of a user's dental arch and a gel or solid oral treatment composition within the tray
Figure 3B:
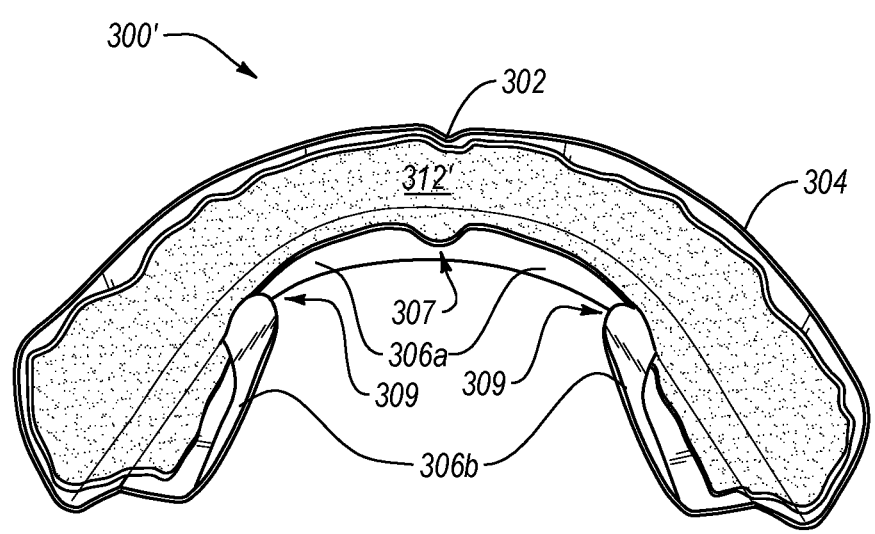

The FIGS. 3A and 3B depict oral treatment devices 300, 300' with features that assist the barrier layers in better conforming to the size and shape of variously dental arches. Instead of continuous sidewalls, oral treatment devices 300, 300' includes a barrier layer 302 having a front sidewall 304, a rear sidewall 306, and a bottom wall 308 interconnecting front sidewall 304 and rear sidewall 306. Rear sidewall 306 further includes a first rear sidewall section 306a that includes a first cut or discontinuity 307 and a second rear sidewall section 306b separated from first rear sidewall section 306a by second cuts or discontinuities 309. The first rear sidewall section 306a is configured to wrap around and lie adjacent to inner surfaces of a person's incisors and canines. Second rear sidewall section 306b is configured to wrap around and contact inner surfaces of a person's bicuspids and optionally one or more molars.

Cuts or discontinuities 309 between first and second sidewall sections 306a, 306b facilitate good fit against a person's incisors and canines, particularly at the junction of the canines and bicuspids. Cuts or discontinuities 309 compensate for the abrupt difference in width between a person's bicuspids adjacent to the second rear sidewall section 306b and the canines adjacent to the first rear sidewall section 306a. Discontinuity or cut 307 in first sidewall section 306a further assists in conforming first sidewall section 306a to inner surfaces of a person's incisors and canines.

FIG. 3A further shows a continuous bead of an oral treatment composition 312 within an interior region or trough defined by front sidewall 304, rear sidewall 306, and bottom wall 308. FIG. 3B alternatively depicts a substantially continuous layer of an oral treatment composition 312' disposed within an interior region or trough defined by front sidewall 304, rear sidewall 306, and bottom wall 308.

Figure 4A:
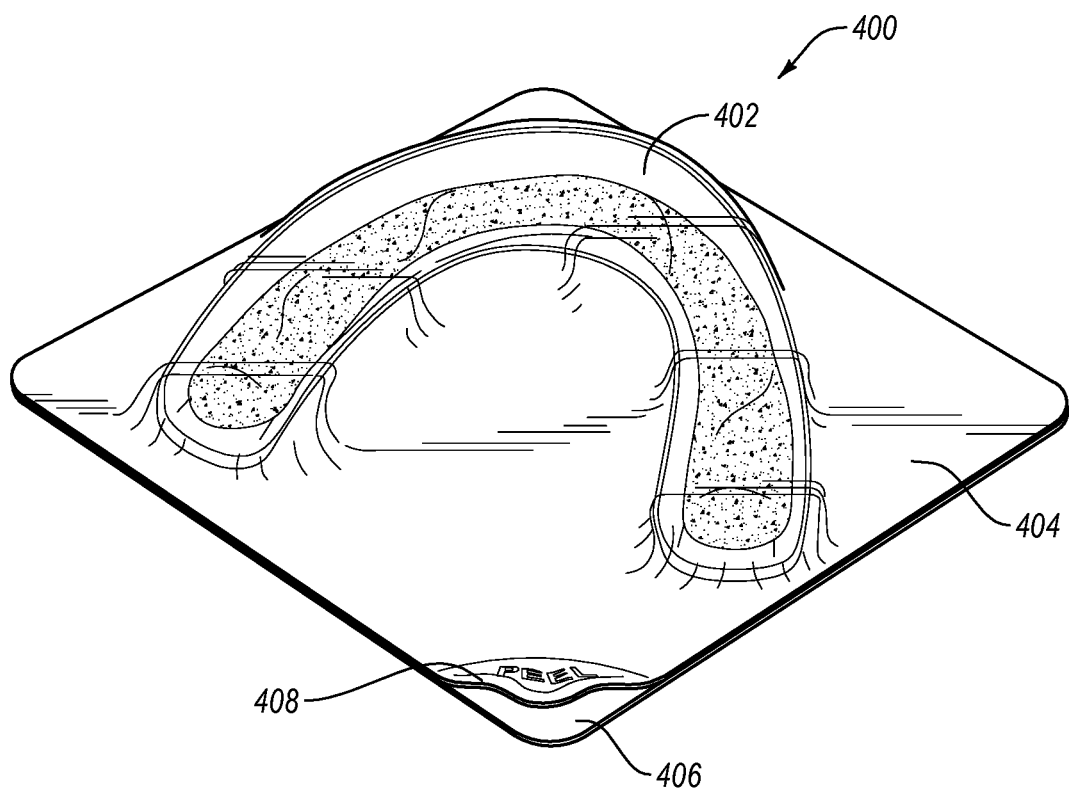
FIGS. 4A-4B illustrate oral treatment devices contained within sealed protective packages having a peelable cover.
Figure 4B:
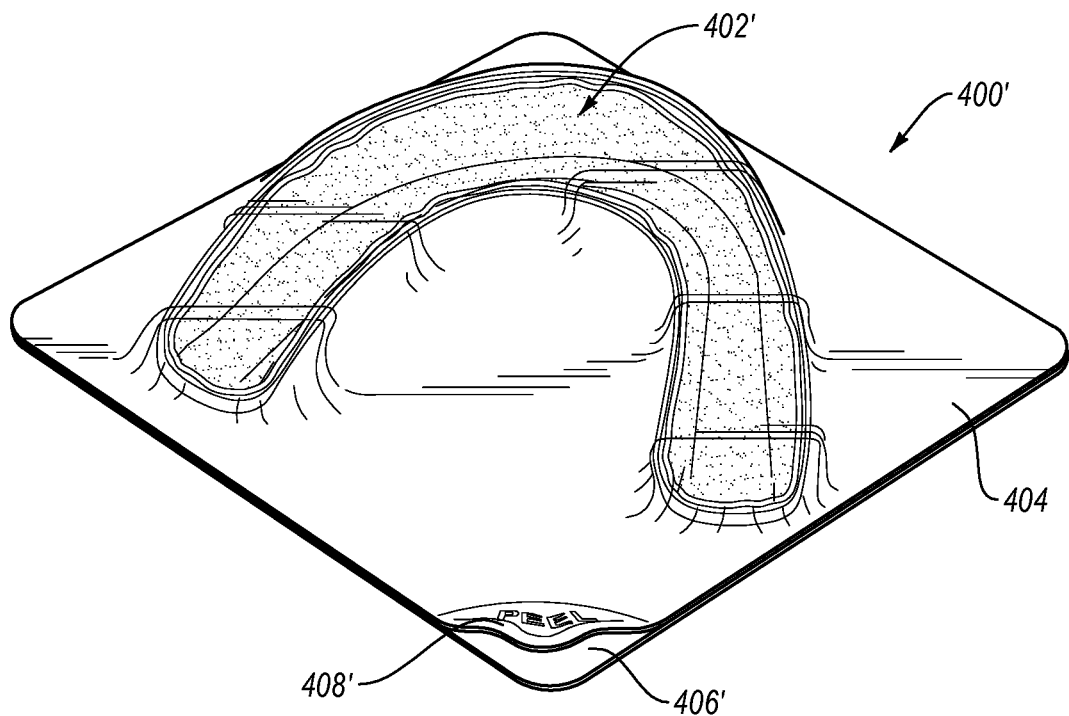

To protect oral treatment devices from contaminants during storage and prior to use, treatment devices can be packaged within a sealed container or package. As illustrated in FIGS. 4A and 4B, exemplary sealed oral treatment packages 400, 400' include an oral treatment device 402, 402' (e.g., dental treatment trays) sealed within a protective package 404, 404'. Protective packages 404, 404' includes a rigid support layer 406, 406' and a peelable cover 408, 408'. When it is desired to use oral treatment device 402, 402', the peelable cover 408, 408' is removed and treatment device 402, 402' is removed or separated from support layer 406, 406'.

FIGS. 5A and 5B depict an embodiment of an oral treatment device in the form of a treatment strip rather than a treatment tray. Oral treatment strip 500 includes a strip of wax-based material 502, which is initially substantially flat and can optionally have rounded corners. Strip of wax-based material 502 may be a single layer of wax-based material comprised of a homogeneous blend of wax and polymer. Coated onto and/or impregnated into strip of wax-based material 502 is an oral treatment composition 504. Oral treatment composition 504 can be a homogeneous material, uniformly and continuously coated onto strip of wax-based material 502.

FIGS. 6A and 6B illustrate an oral treatment device 600 applied to and closely conforming to a surface of a tooth 602. Oral treatment device 600 may include a barrier layer in the form of a dental treatment tray or strip-like sheet that is wrapped around tooth 602 to form a tray-like configuration. Oral treatment device 600 also includes an oral treatment composition that is able to provide a desired treatment to teeth and/or gums. While oral treatment device 600 is shown so that it only covers tooth 602 and not adjacent soft oral tissue 604, it is within the scope of the disclosure for the oral treatment device 600 to extend beyond gingival margin 606 and at least partially overlap soft oral tissue 604.

Figure 7A:
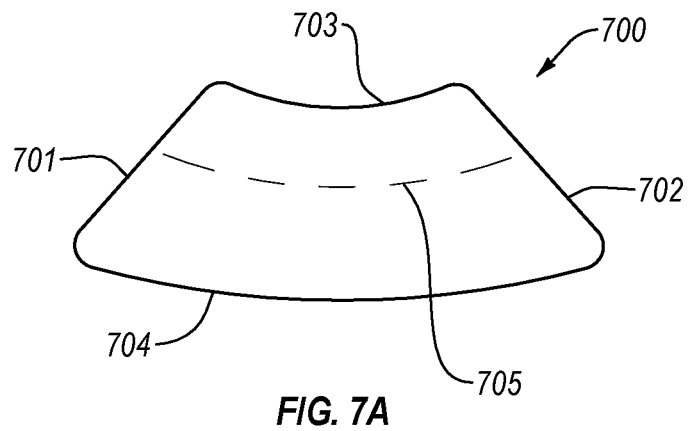
FIGS. 7A-7E illustrate various shapes of strip-like barrier layers that can be used in fashioning oral treatment devices according to the invention.

FIGS. 7A-7E illustrate various embodiments of strip-like barrier layers, which can be placed over a user's teeth and/or gums and adapted so as to wrap around and contact both labial and lingual surfaces. FIG. 7A illustrates an embodiment of a strip of wax-based material 700 that is substantially trapezoidal in shape. Strip 700 has a first side 701, a second side 702, a third side 703, and a fourth side 704. First side 7011 and second side 702 are generally straight sides that angle inward from fourth side 704 toward third side 703. Third side 703 can be concave and shorter then fourth side 704, while fourth side 704 can be convex. In use, fourth side 704 can be placed adjacent to the gingival margin at an intersection between a user's teeth and gums. A fold line 705 may be included in strip 700, which extends from first side 701 to second side 702. Fold line 705 may be located closer to third side 703 or fourth side 704 depending on the desired size and shape of the device when folded during use. Fold line 705 may be determined by the size of a user's teeth and the manner of placement of the oral treatment strip on the user's teeth. Third side 703 will be positioned adjacent to the lingual surfaces of the user's teeth upon folding strip 700 along fold line 705.

Figure 7B:
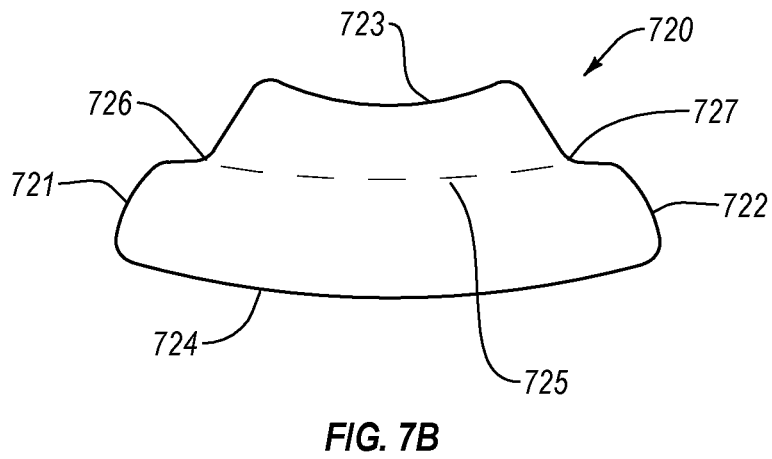

FIG. 7B illustrates another embodiment of a strip of wax-based material 720 that is substantially trapezoidal in shape with stair-stepped sides. Strip 720 has a first side 721, a second side 722, a third side 723, and a fourth side 724. Third side 723 can be concave and shorter then fourth side 724. Fourth side 724 can be convex. First side 721 and second side 722 are both stair step sides that include inner corners 726, 727, respectively. A fold line 725 typically extends between inner corners 726, 727 of the stair steps in first side 721 and second side 722, respectively.

Figure 7C:
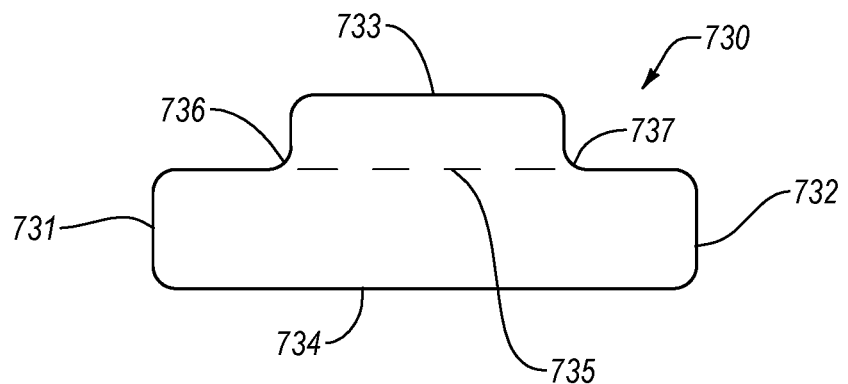

FIG. 7C illustrates an alternative embodiment of a strip of wax-based material 730 that is substantially rectangular in shape with stair-stepped sides. Strip 730 includes a first side 731, a second side 732, a third side 733, and a fourth side 734. First side 731 and second side 732 are both stair step sides that include inner corners 726, 727, respectively. A fold line 735 extends from the corners 736 and 737 of the stair steps in first side 731 and second side 732, respectively. Fold line 35 can be placed over occlusal surfaces of a user's teeth, which permits the strip 700 to fold around and over both the labial and lingual surfaces of the user's teeth. Strip 700 can be placed so that the user's two canine teeth are just outside of corners 736 and 737. Fourth side 734 can be located close to the gingival margin of the front side of a user's teeth. Third side 733 will be located along the lingual surface of the user's teeth.

Figure 7D:
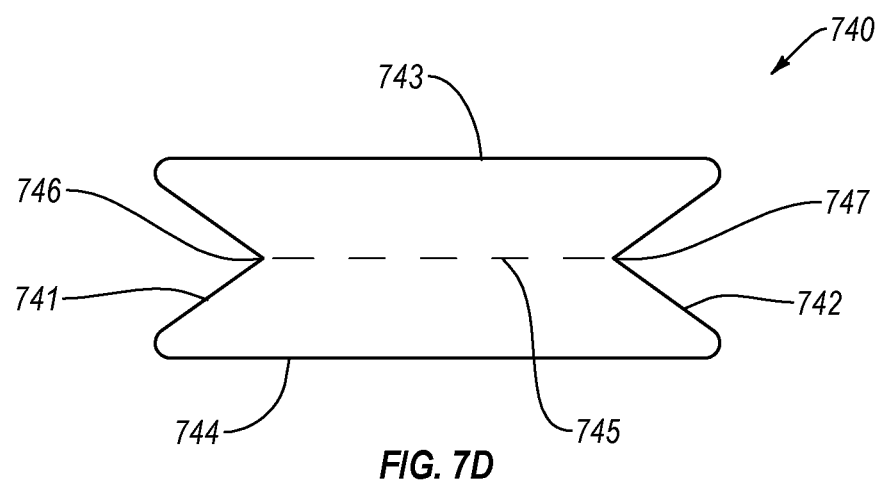

FIG. 7D illustrates an alternative embodiment of a strip of wax-based material 740 that is substantially rectangular in shape but with notched sides. Strip 740 has a first side 741, a second side 742, a third side 743, and a fourth side 744. Third side 743 and fourth side 744 are both substantially straight sides and can be the same length. First side 741 and second side 742 include notches 746, 747, respectively, which enable the occlusal surfaces of a user's canine teeth to not be covered when the strip 740 is placed over the user's teeth. A fold line 745 can extends from notch 746 in first side 741 to notch 747 in second side 742. Notches 746, 747 can have sideways V shapes as shown. However, the notches can be of any desired shape, including rectangular, square, semi circular, oval, and the like and that allow the tips of the canine teeth to not be covered by strip 740 when worn over the user's teeth.

Figure 7E:
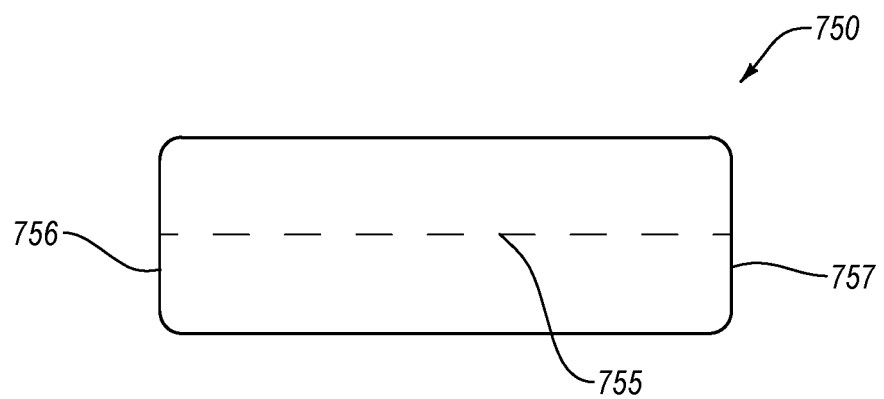

FIG. 7E illustrates an alternative embodiment of a strip of wax-based material 750 that is substantially rectangular in shape but with a fold line 755 between sides 756 and 757 in order to facilitate folding around occlusal edges of a user's teeth during installation.

V. Examples

Following are examples of wax-based compositions that may be used to manufacture oral treatment devices, including dental treatment trays and strip-like barrier layers. The exemplary formulations and manufacturing conditions are given by way of example, and not by limitation. Unless otherwise indicated, all percentages are by weight.

Comparative Example

A sheet of Parafilm® M was thermoformed into a dental treatment tray by heating the sheet to a softening temperature and then vacuum forming the softened sheet over a die having the shape of the dental treatment tray. The resulting dental treatment tray was able to maintain its shape as a tray at room temperature and could be used as a barrier layer in an oral treatment tray. However, the tray lacked thermal stability and lost dimensional stability at temperatures of about 100° F. (about 38° C.) or above. As a result, it was determined that dental treatment trays made by thermoforming Parafilm® M were unsuitable for use in manufacturing oral treatment devices that are subjected to higher temperatures during shipping and storage (i.e., up to 50° C.).

EXAMPLES

The dental trays in the following Examples were or are manufactured by injection molding a wax-based composition as described below. The wax-based composition of each example was or is initially formed by introducing the materials into a twin screw extruder having multiple zones, heating and mixing the materials in the extruder, extruding the composition into a strand, cooling the extruded strand in a water bath, and chopping the strand in to pellets. The pellets were or are then fed into an injection molding machine and injection molded into dental trays. The injection molding machine was configured to initially heat the wax-based composition prior to introduction into the mold cavity and then cool the material to form the solidified trays. The injection molded trays had an average sidewall thickness of about 0.007-0.008 mil (about 0.18-0.2 mm), with thickened occlusal surfaces of about 0.010-0.013 mils (25-33 mm).

Examples 1-10

| Component | Example | | | | | | | | | |
|---|---|---|---|---|---|---|---|---|---|---|
| | 1 | 2 | 3 | 4 | 5 | 6 | 7 | 8 | 9 | 10 |
| Parafilm ® M[1] | 100% | 35% | 30% | 50% | 90% | 95% | 25% | 25% | 25% | 25% |
| Paraffin wax (mp = 167° F.) | | 65% | | | | | 65% | 65% | 65% | 65% |
| Paraffin wax (mp = 149° F.) | | | 70% | | | | | | | |
| Paraffin wax (mp = 181° F.) | | | | 50% | | | | | | |
| Thermoplastic polyolefin elastomer | | | | | 10% | 5% | | | | |
| Distilled wax[2] | | | | | | | 10% | | | |
| Distilled wax[3] | | | | | | | | 10% | | |
| Distilled wax[4] | | | | | | | | | 10% | |
| Distilled wax[5] | | | | | | | | | | 10% |

[1]Proprietary blend of paraffin wax and polyolefin.
[2]Congealing point: 129.5-135.1° C.; start to open point: 115.6-121.2° C.; terminal point: 129.5-135.1° C.; volume of expansion: 16-18%; travel: 6.37-6.89 mm.
[3]Congealing point: 124-129.5° C.; start to open point: 107.3-112.9° C.; terminal point: 126.8-132.3° C.; volume of expansion: 16-18%; travel: 6.37-6.89 mm.
[4]Congealing point: 105.1-106.2° C.; start to open point: 98.4-100.0° C.; terminal point: 114.5-116.2° C.; volume of expansion: 14-16%; travel: 5.88-6.37 mm.
[5]Congealing point: 100-101.2° C.; start to open point: 89.0-90.1° C.; terminal point: 105.6-106.8° C.; volume of expansion: 14-16%; travel: 5.88-6.37 mm.

Dental treatment trays made according to Examples 1-10 had varying levels of thermal stability, plastic deformability, and comfort. All had better thermal stability compared to the thermoformed tray of the Comparative Example, even the injection molded tray of Example 1, which was made by injection molding the composition of Parafilm® M. By way of comparison, the tray of Example 1, made by injection molding 100% Parafilm® M, was dimensionally stabile up to a temperature of about 50-52° C. As the amount of Parafilm® M was reduced and replaced by other components, such as paraffin wax, thermoplastic polyolefin elastomer and/or distilled wax, the temperature stability of the trays increased as did the ability of the trays to be plastically deformable in a user's mouth.

Examples 11-19

| Component | Example | | | | | | | | |
|---|---|---|---|---|---|---|---|---|---|
| | 11 | 12 | 13 | 14 | 15 | 16 | 17 | 18 | 19 |
| Parafilm ® M[1] | 25% | 25% | 25% | 25% | 25% | 25% | 25% | 25% | 25% |
| Paraffin Wax (mp = 167° F.) | | 65% | 65% | 65% | 65% | 64% | 65% | 64% | 65% |
| Distilled wax[2] | | | | | 5% | 8% | | | |
| Distilled wax[3] | | | 5% | 5% | 5% | 3% | 5% | 3% | |
| Distilled wax[4] | | | 5% | | | | | | |
| Distilled wax[5] | | | | 5% | | | 5% | 8% | |
| Distilled wax[6] | | 10% | | | | | | | |
| Distilled wax[7] | | | | | | | | | 10% |

[1]Proprietary blend of paraffin wax and polyolefin.
[2]Congealing point: 129.5-135.1° C.; start to open point: 115.6-121.2° C.; terminal point: 129.5-135.1° C.; volume of expansion: 16-18%; travel: 6.37-6.89 mm.
[3]Congealing point: 124-129.5° C.; start to open point: 107.3-112.9° C.; terminal point: 126.8-132.3° C.; volume of expansion: 16-18%; travel: 6.37-6.89 mm.
[4]Congealing point: 100-101.2° C.; start to open point: 89.0-90.1° C.; terminal point: 105.6-106.8° C.; volume of expansion: 14-16%; travel: 5.88-6.37 mm.
[5]Congealing point: 95.1-96.2° C.; start to open point: 89.5-90.6° C.; terminal point: 100.6-101.7° C.; volume of expansion: 14-16%; travel: 5.88-6.37 mm.
[6]Congealing point: 80.1-81.2° C.; start to open point: 74.5-75.6° C.; terminal point: 85.6-86.7° C.; volume of expansion: 14-16%; travel: 5.88-6.37 mm.
[7]Congealing point: 109-110.6° C.; start to open point: 104-105.6° C.; terminal point: 125.7-127.9° C.; volume of expansion: 15-17%; travel: 6.13-6.63 mm.

Dental treatment trays made according to Examples 11-19 had varying levels of thermal stability, plastic deformability, and comfort. The trays made according to Examples 11-19 had improved thermal stability compared to the tray of the Comparative Example. Reducing the amount of Parafilm® M and replacing it with other components, such as paraffin wax and/or distilled wax, increased temperature stability and the ability of the trays to be plastically deformable in a user's mouth.

Examples 20-28

| Component | Example | | | | | | | | |
|---|---|---|---|---|---|---|---|---|---|
| | 20 | 21 | 22 | 23 | 24 | 25 | 26 | 27 | 28 |
| Propylene-based elastomer[1] | | 22% | | 20% | 20% | 20% | 15% | 30% | 15% |
| Propylene-based elastomer[2] | 22% | | | | | | | | |
| Propylene-based elastomer[3] | | | 22% | | | | | | |

-continued

| Component | Example | | | | | | | | |
|---|---|---|---|---|---|---|---|---|---|
| | 20 | 21 | 22 | 23 | 24 | 25 | 26 | 27 | 28 |
| Microcrystalline Wax[4] | 44% | 44% | 44% | 80% | 60% | 40% | 55% | 40% | 40% |
| Paraffin Wax[5] | 33% | 33% | 33% | | 20% | 40% | 30% | 30% | 45% |

[1]Density: 0.862 g/cm³; MFR (230° C./2.16 kg): 3.0 g/10 min; ethylene content: 16.0 wt %; durometer hardness (Shore A, 15 sec, 23° C.); 67; flexural modulus (23° C.): 11.4 MPa; tensile set (23° C.): 13%; tensile stress at 100% (23° C.): 2.12 MPa; tensile stress at 300% (23° C.): 2.68 MPa; tensile strength at break (23° C.): 13.9 MPa; elongate at break (23° C.): 860%; tear strength (23° C.): 31.0 kN/m; viscat softening temp: 59.0° C.
[2]Density: 0.861 g/cm³; melt index: 7.4 g/10 min; MFR (230° C./2.16 kg): 18 g/10 min; ethylene content: 15.0 wt %; durometer hardness (Shore A, 15 sec, 23° C.); 61; flexural modulus (23° C.): 11.0 MPa; tensile set (23° C.): 13%; tensile stress at 100% (23° C.): 1.70 MPa; tensile stress at 300% (23° C.): 2.10 MPa; tensile strength at break (23° C.): >7.29 MPa; elongate at break (23° C.): >2000%; tear strength (23° C.): 33.0 kN/m; viscat softening temp: 48.0° C.
[3]Density: 0.874 g/cm³; melt index: 0.90 g/10 min; MFR (230° C./2.16 kg): 2.2 g/10 min; ethylene content: 10.5 wt %; Shore A hardness (23° C.); 85; flexural modulus (23° C.): 60.4 MPa; tensile set (23° C.): 49%; tensile stress at 100% (23° C.): 4.40 MPa; tensile stress at 300% (23° C.): 4.50 MPa; tensile strength at break (23° C.): 17.8 MPa; elongate at break (23° C.): 1800%; tear strength (23° C.): 64 kN/m; viscat softening temp: 70.0° C.; peak crystallization temp: 65.0° C.; crystallinity, Hf: 28.0 J/g; crystallization peak, Tc: 64° C.
[4]Drop melt point: 88.9° C. min; kinematic viscosity (100° C.): 16.5 cSt min; oil content: 1.8 wt % max; flash point: 260° C.; ASTM color: 0.5 max; odor: 2 max; needle penetration (25° C.): 10 dmm max.
[5]Congealing point: 66.7-74.4° C.; kinematic viscosity (100° C.): 5.7-7.9 cSt; oil content: 1.0 wt % max; saybolt color: +25 min; needle penetration (25° C.): 18 dmm max; specific gravity (25° C.): 0.927.

Dental treatment trays made according to Examples 20-28 provided improved thermal stability and plastic deformation compared to the tray made according to the Comparative Example.

Examples 29-38

| Component | Example | | | | | | | | | |
|---|---|---|---|---|---|---|---|---|---|---|
| | 29 | 30 | 31 | 32 | 33 | 34 | 35 | 36 | 37 | 38 |
| Propylene-based elastomer[1] | 20% | 20% | 20% | 40% | 30% | 30% | 30% | 35% | 25% | 15% |
| Microcrystalline Wax[2]) | 40% | 60% | 20% | 30% | 35% | 50% | 20% | 33% | 38% | 43% |
| Paraffin Wax[3] | 40% | 20% | 60% | 30% | 35% | 20% | 50% | 33% | 38% | 43% |

[1]Density: 0.861 g/cm³; melt index: 7.4 g/10 min; MFR (230° C./2.16 kg): 18 g/10 min; ethylene content: 15.0 wt %; durometer hardness (Shore A, 15 sec, 23° C.); 61; flexural modulus (23° C.): 11.0 MPa; tensile set (23° C.): 13%; tensile stress at 100% (23° C.): 1.70 MPa; tensile stress at 300% (23° C.): 2.10 MPa; tensile strength at break (23° C.): >7.29 MPa; elongate at break (23° C.).
[2]Drop melt point: 88.9° C. min; kinematic viscosity (100° C.): 16.5 cSt min; oil content: 1.8 wt % max; flash point: 260° C.; ASTM color: 0.5 max; odor: 2 max; needle penetration (25° C.): 10 dmm max.
[3]Congealing point: 66.7-74.4° C.; kinematic viscosity (100° C.): 5.7-7.9 cSt; oil content: 1.0 wt % max; saybolt color: +25 min; needle penetration (25° C.): 18 dmm max; specific gravity (25° C.): 0.927.

Dental treatment trays made according to Examples 29-38 provided improved thermal stability and plastic deformation compared to the tray made according to the Comparative Example.

Examples 39-48

| Component | Example | | | | | | | | | |
|---|---|---|---|---|---|---|---|---|---|---|
| | 39 | 40 | 41 | 42 | 43 | 44 | 45 | 46 | 47 | 48 |
| Thermoplastic elastomer[1] | 20% | 20% | 20% | 40% | 30% | 30% | 30% | 35% | 25% | 22% |
| Microcrystalline Wax[2]) | 40% | 60% | 20% | 30% | 35% | 50% | 20% | 33% | 38% | 39% |
| Paraffin Wax[3] | 40% | 20% | 60% | 30% | 35% | 20% | 50% | 33% | 38% | 39% |

[1]Specific Gravity: 885; density: 0.883 g/cm³; MFR (190° C./2.16 kg): 31 g/10 min; durometer hardness (Shore A, 5 sec): 50; tensile stress (100% strain): 1.54 MPa; tensile stress (300% strain): 2.27 MPa; tensile strength (yield): 6.85 MPa; tensile elongation (break): 800%; tear strength (Die C): 23.6 kN/m; melt viscosity (374° F., 200 sec⁻¹): 136 Pa-s.
[3]Drop melt point: 88.9° C. min; kinematic viscosity (100° C.): 16.5 cSt min; oil content: 1.8 wt % max; flash point: 260° C.; ASTM color: 0.5 max; odor: 2 max; needle penetration (25° C.): 10 dmm max
[4]Congealing point: 66.7-74.4° C.; kinematic viscosity (100° C.): 5.7-7.9 cSt; oil content: 1.0 wt % max; saybolt color: +25 min; needle penetration (25° C.): 18 dmm max; specific gravity (25° C.): 0.927

Dental treatment trays made according to Examples 39-48 provided improved thermal stability and plastic deformation compared to the tray made according to the Comparative Example.

Examples 49-58

| Component | Example | | | | | | | | | |
|---|---|---|---|---|---|---|---|---|---|---|
| | 49 | 50 | 51 | 52 | 53 | 54 | 55 | 56 | 57 | 58 |
| Thermoplastic elastomer[1] | 20% | 20% | 20% | 40% | 30% | 30% | 30% | 35% | 25% | 22% |
| Microcrystalline Wax[3]) | 40% | 60% | 20% | 30% | 35% | 50% | 20% | 33% | 38% | 39% |
| Paraffin Wax[4] | 40% | 20% | 60% | 30% | 35% | 20% | 50% | 33% | 38% | 39% |

[1]Density: 0.890 g/cm$^3$; tensile stress (yield): 10.6 MPa; tensile elongation: 780%; tear strength 16 kN/m; compression set (23° C.): 18%; compression set (70° C.): 35%; compression set (100° C.): 52%; Shore A hardness: 60
[2]Drop melt point: 88.9° C. min; kinematic viscosity (100° C.): 16.5 cSt min; oil content: 1.8 wt % max; flash point: 260° C.; ASTM color: 0.5 max; odor: 2 max; needle penetration (25° C.): 10 dmm max
[3]Congealing point: 66.7-74.4° C.; kinematic viscosity (100° C.): 5.7-7.9 cSt; oil content: 1.0 wt % max; saybolt color: +25 min; needle penetration (25° C.): 18 dmm max; specific gravity (25° C.): 0.927

Dental treatment trays made according to Examples 49-58 provided improved thermal stability and plastic deformation compared to the tray made according to the Comparative Example.

Example 59

Any of the compositions of Examples 2-58 is extruded or otherwise formed into a sheet having a thickness so as to be thermoformable and then formed into a tray using a thermoforming technique known in the art. The trays formed according to Example 59 provide improved thermal stability and plastic deformation compared to the tray made according to the Comparative Example.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A dental tray, comprising:
a composition comprising greater than 40% and up to 95% by weight of a wax component selected from petroleum wax and distilled wax, a thermoplastic elastomer component blended with the wax component, wherein the composition is substantially free of ethylene-vinyl acetate copolymer (EVA),
wherein the thermoplastic elastomer component is an olefin-based elastomer selected from the group consisting of ethylene-, propylene-, and butylene-based elastomers,
wherein the composition is formed into a barrier layer,
wherein the dental tray is plastically deformable at room temperature and thermally stable at a temperature up to at least 40° C.

2. The dental tray of claim 1, wherein the wax component comprises paraffin wax.

3. The dental tray of claim 1, wherein the wax component comprises microcrystalline wax.

4. The dental tray of claim 1, wherein the petroleum wax comprises intermediate wax.

5. The dental tray of claim 1, wherein the dental tray comprises at least one sidewall and a bottom wall adjacent to and extending laterally from the at least one sidewall.

6. The dental tray of claim 1, wherein the dental tray has a thickness in a range of about 0.025 mm to less than 1.5 mm.

7. The dental tray of claim 1, wherein the wax component is homogenously blended with the thermoplastic elastomer component.

8. The dental tray of claim 1, wherein the thermoplastic elastomer component is included in a range of 5% to less than 60% by weight of the composition.

9. The dental tray of claim 1, wherein the wax component is included in a range of 50% to 93% by weight of the composition and the thermoplastic elastomer component is included in a range of 7% to 50% by weight of the composition.

10. The dental tray of claim 1, wherein the olefin-based elastomer is a propylene-based elastomer.

11. The dental tray of claim 1, further comprising a dental treatment composition adjacent to or impregnated within the barrier layer.

12. A dental treatment device, comprising:
a strip formed from a composition comprising greater than 40% and up to 95% by weight of a wax component selected from petroleum wax and distilled wax, a thermoplastic elastomer component blended with the wax component, wherein the composition is substantially free of ethylene-vinyl acetate copolymer (EVA),
wherein the thermoplastic elastomer component is an olefin-based elastomer selected from the group consisting of ethylene-, propylene-, and butylene-based elastomers; and
a dental treatment composition adjacent to or impregnated within the strip,
wherein the strip is plastically deformable at room temperature and thermally stable at a temperature up to at least 40° C.

13. The dental treatment device of claim 12, wherein the wax component comprises at least one of paraffin wax or microcrystalline wax.

14. The dental treatment device of claim 12, wherein the strip is initially flat and sufficiently flexible to be placed over at least a portion of a user's teeth.

15. The dental treatment device of claim 12, wherein the olefin-based elastomer is a propylene-based elastomer.

16. The dental treatment device of claim 12, wherein the dental treatment composition includes a dental bleaching agent.

17. A method of manufacturing a dental treatment device, comprising:

blending a wax component selected from petroleum wax and distilled wax and a thermoplastic elastomer component to form a composition comprising greater than 40% and up to 95% by weight of the wax component, and the thermoplastic elastomer, wherein the composition is substantially free of ethylene-vinyl acetate copolymer (EVA), wherein the thermoplastic elastomer component is an olefin-based elastomer selected from the group consisting of ethylene-, propylene-, and butylene-based elastomers; and forming the composition into a dental treatment tray that is sized and configured to be placed over at least a portion of a user's teeth, wherein the dental treatment tray is plastically deformable at room temperature and thermally stable at a temperature up to at least 40° C.

18. The method of claim 17, wherein the wax component comprises at least one of paraffin wax or microcrystalline wax.

19. The method of claim 17, wherein the forming comprises injection molding or thermoforming the composition into the dental treatment tray having a thickness in a range of about 0.025 mm to less than 1.5 mm.

20. The method of claim 17, further comprising disposing a dental treatment composition on at least one region of the dental treatment tray.

21. A dental treatment device, comprising:

a barrier layer formed from a composition comprising a wax component selected from petroleum wax and distilled wax and a thermoplastic elastomer component, wherein the composition comprises greater than 40% and up to 95% by weight of the wax component, wherein the composition is substantially free of ethylene-vinyl acetate copolymer (EVA), wherein the barrier layer is a dental tray or a strip and has a thickness in a range of about 0.025 mm to less than 1.5 mm; and a dental treatment composition adjacent to or impregnated within the barrier layer, wherein the barrier layer is plastically deformable at room temperature and thermally stable at a temperature up to at least 40° C.

22. The dental tray of claim 1, wherein the dental tray has a thickness in a range of about 0.025 mm to about 1 mm.

23. The dental treatment device of claim 14, wherein the initially flat strip has a thickness in a range of about 0.025 mm to less than 1.5 mm.

24. The method of claim 17, wherein the olefin-based elastomer is a propylene-based elastomer.

25. The dental treatment device of claim 21, wherein the thermoplastic elastomer component is a propylene-based elastomer.

26. The dental treatment device of claim 21, wherein the barrier layer is a flat strip.

27. A method of manufacturing a dental treatment device, comprising:

blending a wax component selected from petroleum wax and distilled wax and a thermoplastic elastomer component to form a composition comprising greater than 40% and up to 95% by weight of the wax component, and the thermoplastic elastomer, wherein the composition is substantially free of ethylene-vinyl acetate copolymer (EVA), wherein the thermoplastic elastomer component is an olefin-based elastomer selected from the group consisting of ethylene-, propylene-, and butylene-based elastomers;

forming the composition into a strip that is sized and configured to be placed over at least a portion of a user's teeth; and disposing a dental treatment composition on at least one region of the strip, wherein the strip is plastically deformable at room temperature and thermally stable at a temperature up to at least 40° C.

* * * * *